(12) United States Patent
Dalva et al.

(10) Patent No.: US 9,012,617 B2
(45) Date of Patent: Apr. 21, 2015

(54) DETECTION REAGENTS FOR TYROSINE KINASE ACTIVITY AND METHODS OF USE THEREOF

(75) Inventors: Matthew Dalva, Narberth, PA (US); Julia X. Zhu, Bern (CH)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/443,953

(22) Filed: Apr. 11, 2012

(65) Prior Publication Data
US 2012/0270240 A1 Oct. 25, 2012

Related U.S. Application Data

(60) Provisional application No. 61/473,847, filed on Apr. 11, 2011.

(51) Int. Cl.
| | | |
|---|---|---|
| *C07H 21/04* | (2006.01) | |
| *C12N 15/09* | (2006.01) | |
| *C12N 5/10* | (2006.01) | |
| *C12Q 1/48* | (2006.01) | |
| *G01N 33/50* | (2006.01) | |
| *G01N 33/58* | (2006.01) | |

(52) U.S. Cl.
CPC ............ *C12Q 1/485* (2013.01); *G01N 33/5044* (2013.01); *G01N 33/582* (2013.01)

(58) Field of Classification Search
CPC ............ G01N 33/582; A61K 49/0017; A61K 49/0045; A61K 49/0047
See application file for complete search history.

(56) References Cited

FOREIGN PATENT DOCUMENTS

| WO | WO 2005/019447 | * | 3/2005 |
| WO | WO 2011/130343 | * | 10/2011 |

OTHER PUBLICATIONS

Kawai et al., Anal. Chem., 76:6144-6149, 2004.*
Robinson et al., Oncogene, 19:5548-4447, 2000.*
Dalva, M., et al. "Rearrangements of synaptic connections in visual cortex revealed by laser photostimulation." Science. Jul. 8, 1994;265(5169):255-8.
Dalva, M., et al. "Cell adhesion molecules: signalling functions at the synapse." Nat Rev Neurosci. Mar. 2007;8 (3):206-20. Epub Feb. 14, 2007.
Dalva, M., et al. "EphB receptors interact with NMDA receptors and regulate excitatory synapse formation." Cell. Dec. 8, 2000;103(6):945-56.
Flanagan, J.G., et al. "The ephrins and Eph receptors in neural development." Annu Rev Neurosci. 1998;21:309-45.
Hirose, K., et al. "Spatiotemporal dynamics of inositol 1,4,5-trisphosphate that underlies complex Ca2+ mobilization patterns." Science. May 28, 1999;284(5419):1527-30.
Honda, A., et al. "Spatiotemporal dynamics of guanosine 3',5'-cyclic monophosphate revealed by a genetically encoded, fluorescent indicator." Proc Natl Acad Sci U S A. Feb. 27, 2001;98(5):2437-42.
Irie, F., et al. "EPHB receptor signaling in dendritic spine development." Front Biosci. May 1, 2004;9:1365-73.
Kaplan, D.R., et al. "Neurotrophin signal transduction in the nervous system." Curr Opin Neurobiol. Jun. 2000;10 (3):381-91.
Katz, L.C., et al. "Scanning laser photostimulation: a new approach for analyzing brain circuits." J Neurosci Methods. Oct. 1994;54(2):205-18.
Kayser, M.S., et al. "EphB receptors couple dendritic filopodia motility to synapse formation." Neuron. Jul. 10, 2008;59 (1):56-69.
Tallini, Y.N., et al. "Imaging cellular signals in the heart in vivo: Cardiac expression of the high-signal Ca2+ indicator GCaMP2." Proc Natl Acad Sci U S A. Mar. 21, 2006;103(12):4753-8. Epub Mar. 13, 2006.
Timar, J., et al. "Antiangiogenic drugs and tyrosine kinases." Anticancer Agents Med Chem. Jun. 2008;8(5):462-9.
Zaccolo, M., et al. "A genetically encoded, fluorescent indicator for cyclic AMP in living cells." Nat Cell Biol. Jan. 2000;2(1):25-9.
Ziv, N.E., et al. "Evidence for a role of dendritic filopodia in synaptogenesis and spine formation." Neuron. Jul. 1996;17 (1):91-102.
Kayser, M.S., et al. "Intracellular and trans-synaptic regulation of glutamatergic synaptogenesis by EphB receptors." J Neurosci. Nov. 22, 2006;26(47):12152-64.
Mattila, P.K., et al. "Filopodia: molecular architecture and cellular functions." Nat Rev Mol Cell Biol. Jun. 2008;9 (6):446-54.
Miyawaki, A., et al. "Fluorescent indicators for Ca2+ based on green fluorescent proteins and calmodulin." Nature. Aug. 28, 1997;388(6645):882-7.
Nakai, J., et al. "A high signal-to-noise Ca(2+) probe composed of a single green fluorescent protein." Nat Biotechnol. Feb. 2001;19(2):137-41.
Oancea, E., et al. "Green fluorescent protein (GFP)-tagged cysteine-rich domains from protein kinase C as fluorescent indicators for diacylglycerol signaling in living cells." J Cell Biol. Feb. 9, 1998;140(3):485-98.
Pawson, T. "Specificity in signal transduction: from phosphotyrosine-SH2 domain interactions to complex cellular systems." Cell. Jan. 23, 2004;116(2):191-203.
Pologruto, P.A., et al. "Monitoring neural activity and [Ca2+] with genetically encoded Ca2+ indicators." J Neurosci. Oct. 27, 2004;24(43):9572-9.
Robles, E., et al. "Focal adhesion kinase signaling at sites of integrin-mediated adhesion controls axon pathfinding." Nat Neurosci. Oct. 2006;9(10):1274-83. Epub Sep. 3, 2006.
Robles, E., et al. "Src-dependent tyrosine phosphorylation at the tips of growth cone filopodia promotes extension." J Neurosci. Aug. 17, 2005;25(33):7669-81.
Songyang, Z., et al. "SH2 domains recognize specific phosphopeptide sequences." Cell. Mar. 12, 1993;72(5):767-78.
Takasu, M.A., et al. "Modulation of NMDA receptor-dependent calcium influx and gene expression through EphB receptors." Science. Jan. 18, 2002;295(5554):491-5. Epub Dec. 20, 2001.

* cited by examiner

*Primary Examiner* — Marianne P Allen
(74) *Attorney, Agent, or Firm* — Kathleen D. Rigaut; Robert C. Netter, Jr.; Dann, Dorfman, Herrell & Skillman

(57) ABSTRACT

Dual colored fluorescent indicators of specific tyrosine kinase activity and methods of use thereof are disclosed.

6 Claims, 13 Drawing Sheets

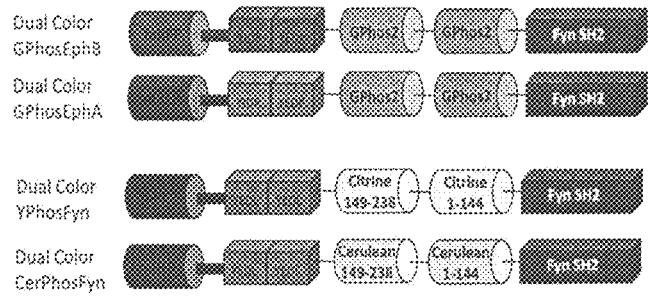
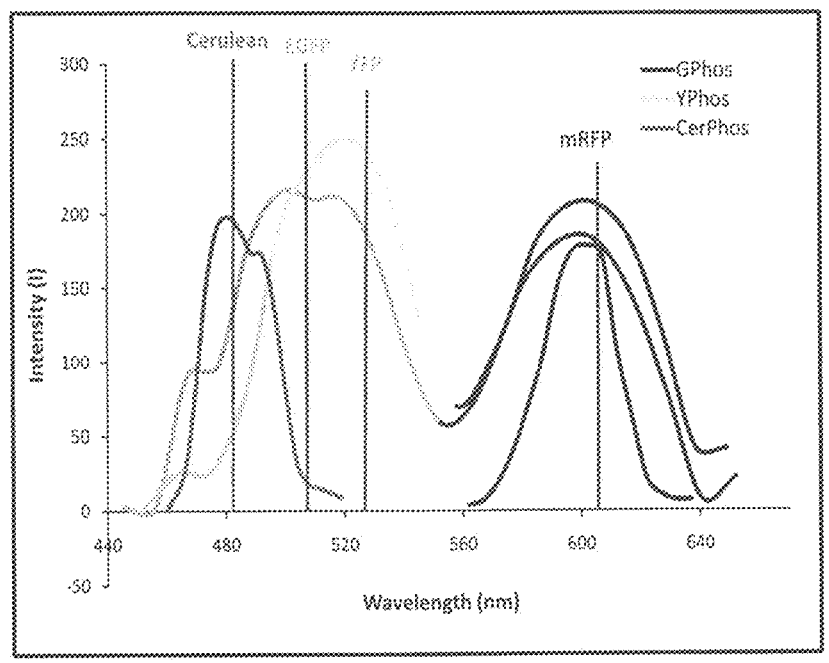
Figure 7

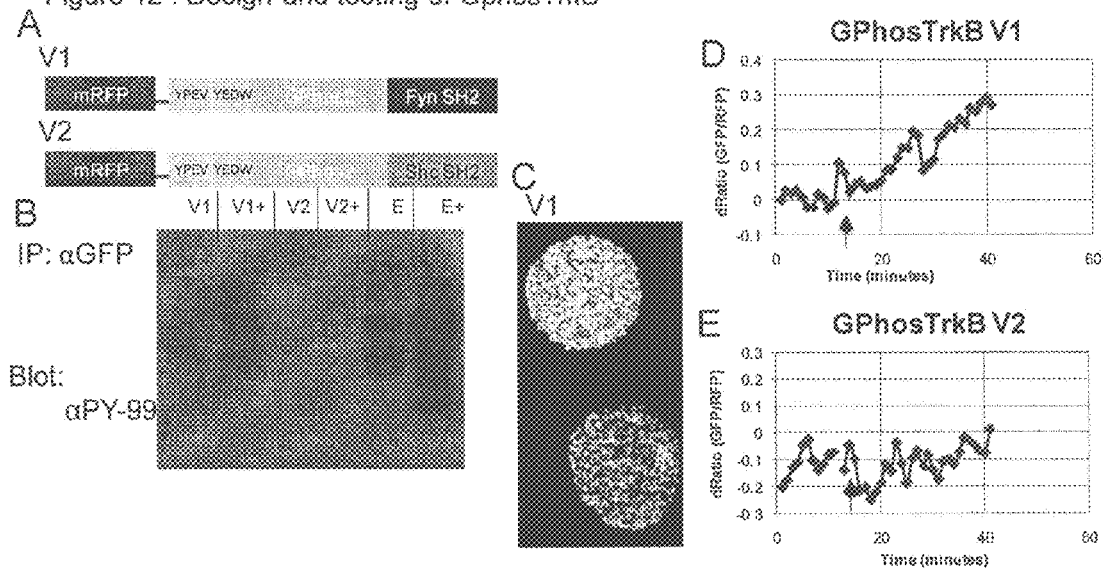

SEQUENCE LISTING

```
<160> NUMBER OF SEQ ID NOS: 92

<210> SEQ ID NO 1
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 1

Gly Ser Tyr Ile Asp Pro Phe Thr Tyr Glu Asp Pro Ala Gly Leu Glu
1               5                   10                  15

<210> SEQ ID NO 2
<211> LENGTH: 48
<212> TYPE: DNA
<213> ORGANISM: Artificial Sequence
<220> FEATURE:
<223> OTHER INFORMATION: Primer

<400> SEQUENCE: 2
ggatcctata tagcccttt cacctatgaa gatcctgccg gcctcgag              48

<210> SEQ ID NO 3
<211> LENGTH: 48
<212> TYPE: DNA
<213> ORGANISM: Artificial Sequence
<220> FEATURE:
```

<223> OTHER INFORMATION: Primer

<400> SEQUENCE: 3
cctaggatat atctgggaaa gtggatactt ctaggacggc cggagctc        48

<210> SEQ ID NO 4
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 4

Gly Ser Tyr Val Asp Pro Phe Thr Tyr Glu Asp Pro Ala Gly Leu Glu
 1               5                  10                  15

<210> SEQ ID NO 5
<211> LENGTH: 48
<212> TYPE: DNA
<213> ORGANISM: Artificial Sequence
<220> FEATURE:
<223> OTHER INFORMATION: Primer

<400> SEQUENCE: 5
ggatcctatg tggatcccctt tacatacgaa gaccccgccg gcctcgag        48

<210> SEQ ID NO 6
<211> LENGTH: 48
<212> TYPE: DNA
<213> ORGANISM: Artificial Sequence
<220> FEATURE:
<223> OTHER INFORMATION: Primer

<400> SEQUENCE: 6
cctaggatac acctagggaa atgtatgctt ctggggcggc cggagctc        48

<210> SEQ ID NO 7
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 7

Gly Ser Tyr Thr Asp Leu Val Gly Glu Ile Tyr Glu Asp Leu Met Gly
 1               5                  10                  15

Leu Glu

<210> SEQ ID NO 8
<211> LENGTH: 54
<212> TYPE: DNA
<213> ORGANISM: Artificial Sequence
<220> FEATURE:
<223> OTHER INFORMATION: Primer

<400> SEQUENCE: 8
ggatcctaca ctgacctggt tggtgaaatc tacgaagact tgatgggcct cgag        54

<210> SEQ ID NO 9
<211> LENGTH: 54
<212> TYPE: DNA
<213> ORGANISM: Artificial Sequence
<220> FEATURE:
<223> OTHER INFORMATION: Primer

<400> SEQUENCE: 9

```
cctaggatgt gactggacca accactttag atgcttctga actacccgga gctc        54
```

<210> SEQ ID NO 10
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 10

Gly Ser Glu Leu Gly Ala Pro Asn Tyr Pro Glu Val Leu Tyr Glu Asp
 1               5                  10                  15

Trp Thr Thr Gly Ala Leu Glu
            20

<210> SEQ ID NO 11
<211> LENGTH: 69
<212> TYPE: DNA
<213> ORGANISM: Artificial Sequence
<220> FEATURE:
<223> OTHER INFORMATION: Primer

<400> SEQUENCE: 11

```
ggatccgagc tcggtgctcc aaattaccct gaagtcctct atgaagactg gaccacgggt        60
gctctcgag                                                                69
```

<210> SEQ ID NO 12
<211> LENGTH: 69
<212> TYPE: DNA
<213> ORGANISM: Artificial Sequence
<220> FEATURE:
<223> OTHER INFORMATION: Primer

<400> SEQUENCE: 12

```
cctaggctcg agccacgagg tttaatggga cttcaggaga tacttctgac ctggtgccca        60
cgagagctc                                                                69
```

<210> SEQ ID NO 13
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 13

Gly Ser Glu Leu Gly Ala Asp Asp Tyr Ala Glu Ile Ile Asp Glu Glu
 1               5                  10                  15

Asp Thr Tyr Thr Met Pro Ser Thr Gly Ala Leu Glu
            20                  25

<210> SEQ ID NO 14
<211> LENGTH: 84
<212> TYPE: DNA
<213> ORGANISM: Artificial Sequence
<220> FEATURE:
<223> OTHER INFORMATION: Primer

<400> SEQUENCE: 14

```
ggatccgagc tcggtgctga tgactatgca gagatcatcg atgaggaaga cacatacacc        60
atgccctcga ccggtgctct cgag                                               84
```

<210> SEQ ID NO 15

```
<211> LENGTH: 84
<212> TYPE: DNA
<213> ORGANISM: Artificial Sequence
<220> FEATURE:
<223> OTHER INFORMATION: Primer

<400> SEQUENCE: 15
cctaggctcg agccacgact actgatacgt ctctagtagc tactccttct gtgtatgtgg      60
tacgggagct ggccacgaga gctc                                             84

<210> SEQ ID NO 16
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 16

Gly Ser Asp Arg Leu His Pro Asn Pro Met Tyr Gln Arg Leu Gly Asn
 1               5                  10                  15

Asn Ile Glu Tyr Val Arg Asp Leu Glu
            20                  25

<210> SEQ ID NO 17
<211> LENGTH: 76
<212> TYPE: DNA
<213> ORGANISM: Artificial Sequence
<220> FEATURE:
<223> OTHER INFORMATION: Primer

<400> SEQUENCE: 17
ggatccgaca gacttcatcc caaccccatg taccagcgac tggggaaaca acattgaata      60
tgtccgtgat ctcgag                                                      76

<210> SEQ ID NO 18
<211> LENGTH: 76
<212> TYPE: DNA
<213> ORGANISM: Artificial Sequence
<220> FEATURE:
<223> OTHER INFORMATION: Primer

<400> SEQUENCE: 18
cctaggctgt ctgaagtagg gttggggtac atggtcgctg accccttgtt gtaacttat       60 acaggcacta gagctc                                                      76

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
acgcgtggtt acattcccag caattacg                                         28

<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20
ttgtacccca caaacttctg gaggaccggt gcggccgc                              38
```

<210> SEQ ID NO 21
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 21

Leu Ala Glu Ala Ala Ala Lys Glu Ala Ala Lys Glu Ala Ala Ala
 1               5                  10                  15
Lys Glu Ala Ala Ala Lys Glu Ala Ala Ala Lys Ala Ala Ala
            20                  25                  30

<210> SEQ ID NO 22
<211> LENGTH: 102
<212> TYPE: DNA
<213> ORGANISM: Artificial Sequence
<220> FEATURE:
<223> OTHER INFORMATION: Primer

<400> SEQUENCE: 22
gatctgtcga cttagctgaa gctgctgcta aagaagctgc tgctaaagaa gctgctgcta      60
aagaagctgc tgctaaagaa gctgctgcta agctgctgc tg                        102

<210> SEQ ID NO 23
<211> LENGTH: 102
<212> TYPE: DNA
<213> ORGANISM: Artificial Sequence
<220> FEATURE:
<223> OTHER INFORMATION: Primer

<400> SEQUENCE: 23
gatccagcag cagctttagc agcagcttct ttagcagcag cttctttagc agcagcttct      60
ttagcagcag cttctttagc agcagcttca gctaagtcga ca                       102

<210> SEQ ID NO 24
<211> LENGTH: 39
<212> TYPE: DNA
<213> ORGANISM: Artificial Sequence
<220> FEATURE:
<223> OTHER INFORMATION: Primer

<400> SEQUENCE: 24
agatctgatc tgccgccacc atggcctcct ccgaggacg                            39

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
ctccaccggc gccgtcgac                                                  19

<210> SEQ ID NO 26
<211> LENGTH: 25
<212> TYPE: DNA
<213> ORGANISM: Artificial Sequence
<220> FEATURE:
<223> OTHER INFORMATION: Primer

<400> SEQUENCE: 26

```
ctcgagaacg ccatcagcga caacg                                         25

<210> SEQ ID NO 27
<211> LENGTH: 40
<212> TYPE: DNA
<213> ORGANISM: Artificial Sequence
<220> FEATURE:
<223> OTHER INFORMATION: Primer

<400> SEQUENCE: 27
ctcgagggtg gatacaacag ccacaacgtc tatatcatgg                         40

<210> SEQ ID NO 28
<211> LENGTH: 29
<212> TYPE: DNA
<213> ORGANISM: Artificial Sequence
<220> FEATURE:
<223> OTHER INFORMATION: Primer

<400> SEQUENCE: 28
gcatggacga gctgtacaag ggcggtacc                                     29

<210> SEQ ID NO 29
<211> LENGTH: 34
<212> TYPE: DNA
<213> ORGANISM: Artificial Sequence
<220> FEATURE:
<223> OTHER INFORMATION: Primer

<400> SEQUENCE: 29
ggtaccggag ggagcgtgag caagggcgag gagc                               34

<210> SEQ ID NO 30
<211> LENGTH: 34
<212> TYPE: DNA
<213> ORGANISM: Artificial Sequence
<220> FEATURE:
<223> OTHER INFORMATION: Primer

<400> SEQUENCE: 30
ggggcacaag ctggagtaca acggtggaac gcgt                               34

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
gcatcaaggc gaacttcaag atcc                                          24

<210> SEQ ID NO 32
<211> LENGTH: 14
<212> TYPE: DNA
<213> ORGANISM: Artificial Sequence
<220> FEATURE:
<223> OTHER INFORMATION: Primer

<400> SEQUENCE: 32
ggacggcggc gtgc                                                     14

<210> SEQ ID NO 33
<211> LENGTH: 17
<212> TYPE: DNA
<213> ORGANISM: Artificial Sequence
```

<220> FEATURE:
<223> OTHER INFORMATION: Primer

<400> SEQUENCE: 33
gctcgcctac cactacc                                                17

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
ccagtccaag ctgagcaaag acc                                         23

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
cgaaggctac atccaggagc                                             20

<210> SEQ ID NO 36
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 36

Gly Ser Ser Lys Ser Lys Pro Lys Asp Pro Ser Gln Arg Arg Arg
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 37

Gly Gly Gly Gly Ser Gly Gly Gly Gly Ser Gly Gly Gly Gly Ser
 1               5                  10                  15

<210> SEQ ID NO 38
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 38

Gly Gly Gly Gly Ser Gly Gly Gly Gly Ser Gly Gly Gly Gly Ser Gly
 1               5                  10                  15

Gly Gly Gly Ser
            20

<210> SEQ ID NO 39
<211> LENGTH: 42
<212> TYPE: DNA
<213> ORGANISM: Artificial Sequence
<220> FEATURE:

<223> OTHER INFORMATION: Primer

<400> SEQUENCE: 39
agatctgata tcgccgccac catggtgagc aagggcgagg ag                42

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
ggcatggacg agctgtacaa ggtcgac                                 27

<210> SEQ ID NO 41
<211> LENGTH: 4
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 1

<400> SEQUENCE: 41

Tyr Glu Glu Ile
 1

<210> SEQ ID NO 42
<211> LENGTH: 4
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 1
<220> FEATURE:
<221> NAME/KEY: VARIANT
<222> LOCATION: (2)...(3)
<223> OTHER INFORMATION: Xaa = any amino acid

<400> SEQUENCE: 42

Tyr Xaa Xaa Met
 1

<210> SEQ ID NO 43
<211> LENGTH: 12
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 1, 9

<400> SEQUENCE: 43

Tyr Thr Asp Leu Val Gly Glu Ile Tyr Glu Asp Leu
 1               5                  10

<210> SEQ ID NO 44
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION

<222> LOCATION: 4

<400> SEQUENCE: 44

Glu Pro Gln Tyr Gln Pro Gly Glu Asn
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 5

<400> SEQUENCE: 45

Thr Glu Gly Gln Tyr Gln Pro Gln Pro
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 46

Glu Gly Gln Tyr Gln Gln Gln Pro
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 47

Thr Asp Asp Tyr Ala Glu Ile Ile Asp
1               5

<210> SEQ ID NO 48
<211> LENGTH: 11
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4, 6

<400> SEQUENCE: 48

Leu Ile Leu Tyr Ala Tyr Gln Leu Ser Thr Ala
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Sequence
<220> FEATURE:

<221> NAME/KEY: PHOSPHORYLATION
<222> LOCATION: 3

<400> SEQUENCE: 49

Cys Thr Tyr Glu Ala Met Tyr Asn Ile Gln
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 5

<400> SEQUENCE: 50

Pro Glu Lys Val Tyr Glu Leu Met Arg
1               5

<210> SEQ ID NO 51
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 2, 8

<400> SEQUENCE: 51

Ile Tyr Ile Asp Pro Phe Thr Tyr Glu Asp Pro Asn Glu
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 2, 8

<400> SEQUENCE: 52

Val Tyr Ile Asp Pro Phe Thr Tyr Glu Asp Pro Asn Glu
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 1, 2, 8

<400> SEQUENCE: 53

Tyr Tyr Ile Asp Pro Ser Thr Tyr Glu Asp Pro Asn Glu
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Sequence

```
<220> FEATURE:
<221> NAME/KEY: PHOSPHORYLATION
<222> LOCATION: 1, 7

<400> SEQUENCE: 54

Tyr Val Asp Pro Phe Thr Tyr Glu Asp Pro
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 3, 9

<400> SEQUENCE: 55

Leu Lys Tyr Val Asp Leu Gln Ala Tyr Glu Asp Pro Ala Gln
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 6

<400> SEQUENCE: 56

Ile Glu Asn Pro Gln Tyr Phe Ser Asp Ala
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 2, 6, 7

<400> SEQUENCE: 57

Ile Tyr Ser Thr Asp Tyr Tyr Arg Val Gly
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 58

Pro Pro Val Tyr Leu Asp Val Leu Gly
1               5

<210> SEQ ID NO 59
<211> LENGTH: 9
<212> TYPE: PRT
<213> ORGANISM: Artificial Sequence
<220> FEATURE:
```

<223> OTHER INFORMATION: Synthetic Sequence
<220> FEATURE:
<221> NAME/KEY: PHOSPHORYLATION
<222> LOCATION: 6

<400> SEQUENCE: 59

Ile Glu Asn Pro Gln Tyr Phe Gly Ile
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 2, 6, 7

<400> SEQUENCE: 60

Val Tyr Ser Thr Asp Tyr Tyr Arg Val Gly
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 61

Ser Pro Val Tyr Leu Asp Ile Leu Gly
1               5

<210> SEQ ID NO 62
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 6

<400> SEQUENCE: 62

Ile Glu Asn Pro Gln Tyr Phe Arg Gln Gly
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 1, 5, 6

<400> SEQUENCE: 63

Tyr Ser Thr Asp Tyr Tyr Arg Leu Phe Asn
1               5                   10

<210> SEQ ID NO 64
<211> LENGTH: 9
<212> TYPE: PRT
<213> ORGANISM: Artificial Sequence

```
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 64

Thr Pro Ile Tyr Leu Asp Ile Leu Gly
 1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 65

Asn Cys Thr Tyr Gly Cys Ala Gly Pro
 1               5

<210> SEQ ID NO 66
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 5

<400> SEQUENCE: 66

Gly Pro Asp Tyr Tyr Glu Val Glu Glu Asp
 1               5                  10

<210> SEQ ID NO 67
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 67

Leu Gln Arg Tyr Ser Ser Asp Pro Thr
 1               5

<210> SEQ ID NO 68
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 68

Gln Pro Glu Tyr Val Asn Gln Pro Asp Val
 1               5                  10

<210> SEQ ID NO 69
<211> LENGTH: 10
<212> TYPE: PRT
```

-continued

<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 69

Asn Gln Glu Tyr Leu Asp Leu Ser Ile Pro
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4, 6

<400> SEQUENCE: 70

Gly Leu Glu Tyr Cys Tyr Asn Pro Ser
1               5

<210> SEQ ID NO 71
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 71

Val Ser Glu Tyr Glu Leu Pro Glu Asp Pro
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 72

Gly Pro Leu Tyr Val Ile Val Glu Tyr Ala
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 73

Asn Glu Glu Tyr Leu Asp Leu Thr Gln Pro
1               5                   10

<210> SEQ ID NO 74
<211> LENGTH: 10

```
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 74

Val Ser Glu Tyr Glu Leu Pro Glu Asp Pro
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 75

Gly Pro Leu Tyr Val Ile Val Glu Tyr Ala
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 76

His Asp Leu Tyr Met Ile Met Arg Glu
1               5

<210> SEQ ID NO 77
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 77

Thr Asp Glu Tyr Leu Asp Leu Ser Val Pro
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4, 6

<400> SEQUENCE: 78

Gly His Glu Tyr Ile Tyr Val Asp Pro Val Gln
1               5                   10

<210> SEQ ID NO 79
```

```
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 79

Asp Ser Asn Tyr Ile Ser Lys Gly Ser
 1               5

<210> SEQ ID NO 80
<211> LENGTH: 12
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 7

<400> SEQUENCE: 80

Asn Glu Gly Asp Asn Asp Tyr Ile Ile Pro Leu Pro
 1               5                  10

<210> SEQ ID NO 81
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 81

Ser Ile Asp Tyr Val Pro Met Leu Asp
 1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 82

Ile Thr Glu Tyr Cys Arg Tyr Gly Asp Leu
 1               5                  10

<210> SEQ ID NO 83
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 83

Ala Asp Pro Tyr Ile Thr Pro Glu Met
 1               5
```

```
<210> SEQ ID NO 84
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 84

Lys Phe His Tyr Asp Asn Thr Ala
 1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 85

Pro Gly Glu Tyr Val Asn Ile Glu Phe
 1               5

<210> SEQ ID NO 86
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: PHOSPHORYLATION
<222> LOCATION: 4

<400> SEQUENCE: 86

Ser Leu Asn Tyr Ile Asp Leu Asp Leu Ala
 1               5                  10

<210> SEQ ID NO 87
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 87

Tyr Glu Asp Leu
 1

<210> SEQ ID NO 88
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 88

Tyr Ile Asp Pro
 1

<210> SEQ ID NO 89
<211> LENGTH: 4
<212> TYPE: PRT
<213> ORGANISM: Artificial Sequence
<220> FEATURE:
```

```
<223> OTHER INFORMATION: Synthetic Sequence

<400> SEQUENCE: 89

Tyr Glu Asp Pro
1

<210> SEQ ID NO 90
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 90

Tyr Val Asp Pro
1

<210> SEQ ID NO 91
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 91

Tyr Pro Glu Val
1

<210> SEQ ID NO 92
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 92

Tyr Glu Asp Trp
1
```

DETECTION REAGENTS FOR TYROSINE KINASE ACTIVITY AND METHODS OF USE THEREOF

This application claims priority to U.S. Provisional Application No. 61/473,847 filed Apr. 11, 2011, the entire contents being incorporated herein by reference as though set forth in full.

FIELD OF THE INVENTION

The invention is directed to rapid and quantitative assay systems for detecting the activity of specific tyrosine kinase enzymes in vivo and in vitro. Specifically, sensitive fluorescent ratiometric indicator reagents are disclosed which facilitate visualization and quantitation of increases and decreases of tyrosine kinase activity in real time. The assays and reagents of the invention can be used to identify test compounds for use in therapeutic applications in those diseases where tyrosine kinase activity plays a pathological role.

BACKGROUND OF THE INVENTION

Several publications and patent documents are cited throughout the specification in order to describe the state of the art to which this invention pertains. Each of these citations is incorporated by reference herein as though set forth in full.

Activation of tyrosine kinases transmits extracellular cues to signal transduction cascades that result in a diverse set of adaptive events, while misregulation of tyrosine kinase signaling is prominent in many diseases. Clearly, the spatial and temporal dynamics of tyrosine kinase activity is fundamental to determining its diverse downstream effects.

Understanding neuronal plasticity, development, and function will increasingly depend on the ability to probe signaling events at the single cell and sub-cellular levels in living tissues and organisms. In the last twenty years, dye-based and genetically encoded calcium indicators that allow neuronal activity and calcium influx to be monitored in living neurons have substantially advanced our understanding of neuronal function. During the next twenty years genetically encoded tools for dissecting cell signaling in live cells will likely have even greater impact.

Initiation of intracellular signaling typically begins when transmembrane receptor molecules bind soluble or membrane attached ligands. Receptor tyrosine kinases (RTKs) are one of the most studied and prevalent classes of receptor proteins and include many molecules with prominent roles in neuronal development and plasticity including Trk and Eph receptors (Flanagan and Vanderhaeghen, 1998; Kaplan and Miller, 2000). Overall, there are approximately 20 families of these kinases that mediate events from cell differentiation, synapse formation, synaptic plasticity and cell survival. Precise activation of receptor TKs is important for specifying the biological outcome of their signaling while over-activation can result in diseases such as cancer. Normally, kinase activity of these proteins is induced by simple ligand induced dimerization (Trks) or multimerization (Ephs). However, we have little understanding of the fine-scale subcellular dynamic regulation of these molecules.

It is clear a need exists in the art for tyrosine kinase activity detection reagents. Ideally such reagents would be sensitive enough to correlate activity with specific tyrosine kinase action in real time.

SUMMARY OF THE INVENTION

Tyrosine kinase activity has been shown to be critical for proper neuronal development and for the growth and progression of some cancerous tumors. There are over 90 known tyrosine kinases, whose activities play a role in the regulation of numerous cellular functions including cell growth, proliferation, and metabolism. Despite the importance of tyrosine kinases and their subsequent phosphorylation events, there remains the need for an effective research tool to examine the spatial and temporal dynamics of tyrosine kinase activity at a subcellular level. To satisfy this need, novel, dual colored fluorescent indicators of specific tyrosine kinase activity have been generated. These indicator molecules facilitate further investigation of tyrosine kinase activity in different model systems. Notably, indicators can be constructed such that they are specific for different tyrosine kinases. Additionally, the dual colored ratiometric system disclosed allows users to control for non-specific changes in cell fluorescence and shape and allows for real-time detection of increases or decreases in specific tyrosine kinase activity at a subcellular level. Finally, the system enables simultaneous measurement of multiple different kinase activities.

Thus, in accordance with the present invention, a series of genetic constructs encoding dual colored, specific, tyrosine kinase enzyme indicator molecules are provided. Exemplary constructs comprise at least the following sequences in operable linkage: a) promoter sequence effective to drive expression of said construct in a target cell; b) a sequence encoding a first fluorescent reporter molecule that is insensitive to changes in phosphorylation; c) sequences encoding at least two distinct phospho-peptides which are substrates of at least two different tyrosine kinases; d) a sequence encoding a circularly permuted second fluorescent reporter molecule, said first and second reporter molecules being different and said second reporter being sensitive to specific phosphorylation events; and e) an SH2 interacting domain. In order to confer enzyme specificity to the constructs, the pair of phophopeptides and SH2 interacting domains in the construct may be substituted one or another. Exemplary peptides for this purpose are selected from the group of phospho-peptides comprising the specific phosphorylation domains and the SH2 interacting domains provided in Table 1. The specific constructs shown in the schematic diagrams in FIG. 1 and FIG. 12 comprise preferred embodiments of the invention. Such constructs can also be cloned into appropriate expression vectors for expression in host cells of interest. Such vectors and host cells are also encompassed by the present invention.

In yet another aspect, an assay for screening a test agent for the ability to modulate activity of a specific protein tyrosine kinase involved in signal transduction in a cell is provided. An exemplary assay entails incubating a host cell comprising the constructs of the invention in the presence and absence of said agent under conditions and for a time sufficient to allow for kinase activity to occur and imaging said cells at specified time intervals and quantifying alterations in fluorescence generated from the second fluorescence reporter relative to said first reporter thereby visualizing and quantifying specific tyrosine kinase activity in real time whereby differences in the fluorescence ratio in the presence and absence of said agent is indicative of an agent that modulates the activity of the tyrosine kinase being assayed. In a preferred embodiment, the assay is performed in a microtiter plate.

Finally, the invention also encompasses a kit containing components for practicing the assay method described herein.

BRIEF DESCRIPTION OF THE DRAWINGS

FIG. 7: Design of GPhos and YPhos. A) Schematic of Gphosfyn and YPhosfyn. YEDL (SEQ ID NO: 87), YIDP (SEQ ID NO: 88), and YEDP (SEQ ID NO: 89) are shown. B) Lambda scan of emission spectra for CPhos, GPhos and YPhos in HEK293 Ts co-transfected with mRFP.

FIG. 12: Design and testing of GphosTrkB indicators: A. Design of GphosTrkB (V1 and V2). V1 has a similar design to other Gphos probes with a fyn SH2 domain. V2 consists of the same fluorescent domains and phosphorylation site as other Gphos probes, but has a Shc SH2 domain replacing the fyn SH2 domain. YPEV (SEQ ID NO: 91) and YEDW (SEQ ID NO: 92) are shown. B) Western blot of immunoprecipitation of GphosTrkBV1 and V2 with (+) and without (−) stimulation by the trkB ligand BDNF. IP conducted with anti-GFP antibodies and the blot was probed with anti-PY-99 antibodies. C. Example of HEK293 cells labeled with Gphos-TrkB. D. Quantification of the effects of stimulating HEK293T cells transfected with trkB and GphosTrkBV1. E. As in D, but cells were transfected with GphosTrkBV2.

DETAILED DESCRIPTION OF THE INVENTION

Figure 1:
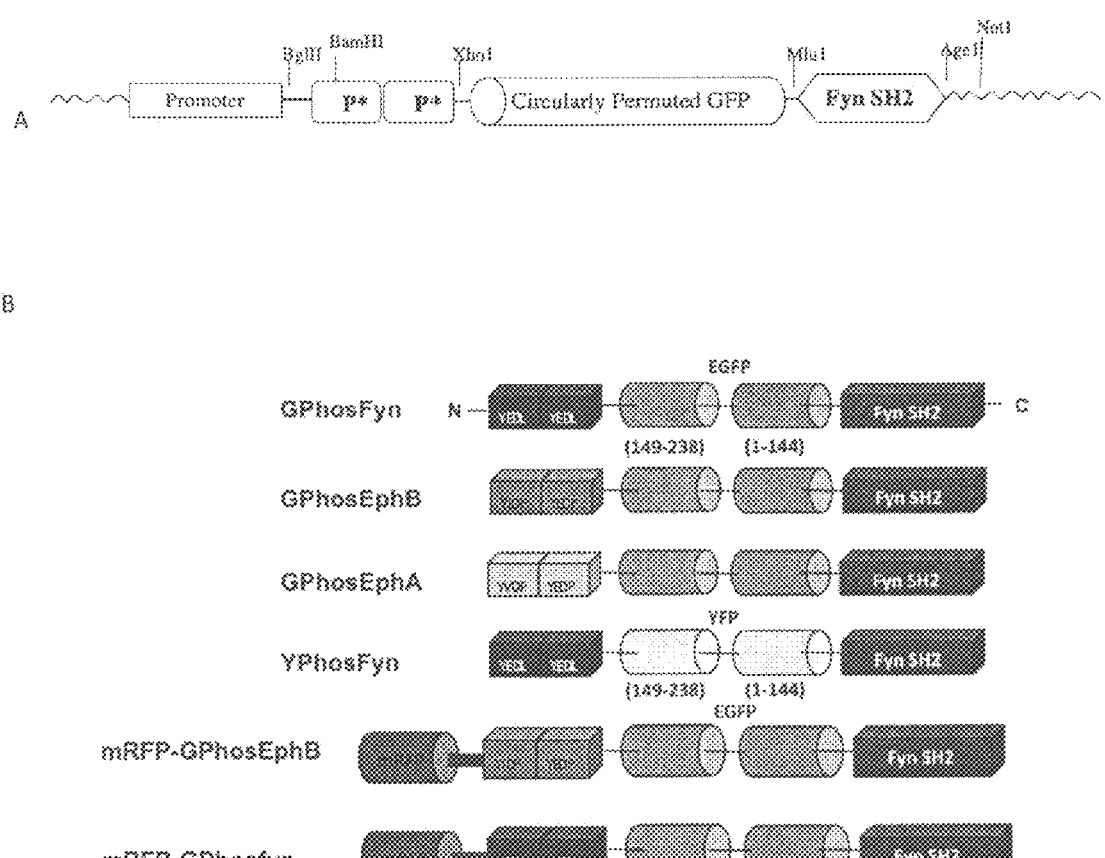
FIG. 1: Design of GPhos and YPhos. A) Each domain of GPhos indicator system can be removed by cutting with two efficient enzymes. BglII-Xho1 sites flank the phospho-peptide. Xho1-MluI sites flank the fluorescent molecule. The binding element (shown as Fyn SH2) is flanked by MluI-Age1. B) Schematic representation of various Phos indicators that we have already developed and tested. Phospho-peptide region, circularly permuted YFP and EGFP, mRFP, and Fyn SH2 domain are shown. YEDL (SEQ ID NO: 87), YIDP (SEQ ID NO: 88), YEDP (SEQ ID NO: 89), and YVDP (SEQ ID NO: 90) are shown. C) Construct maps of the indicators showing appropriate restriction sites for insertion of relevant components for detection and quantification of tyrosine kinase (TK) activity.

In accordance with the present invention, dual color vector-encoded phosphorylation imaging indicators for detecting the level and changes (increase or decrease) in specific tyrosine kinase phosphorylation events in living cells are disclosed. The encoded fusion protein indicators consist of an N-terminal first fluorescent protein that is insensitive to protein phosphorylation operably linked to at least two consensus sequences for tyrosine phosphorylation, a circularly permuted cyan, green or yellow fluorescent protein responsive to a phosphorylation event on said consensus sequence, and a C-terminal SH2 domain.

Constructs have been made specific for the activities of fyn, EphA, and EphB. These have been made with both permutated GFP and YFP and with the addition of the phosphorylation insensitive mRFP molecule. A single colored GPhos-Fyn construct has been tested by transfection into the HEK293 cell line, showing increases and decreases in fluorescence in response to pharmacological manipulation. Furthermore, the GPhos-EphB construct effectively detects increases in EphB activity when transfected into cortical neurons. Preferred constructs encoding the TK indicators of the invention are provided in FIG. 1 and FIG. 12. However modifications to these vectors as provided in Example I are also encompassed by the present invention.

The following advantages are provided by the reagents disclosed herein.
1) Specificity for individual tyrosine kinase activities;
2) Dual colored ratiometric system allows users to control for non-specific changes in cell fluorescence and shape and accurately measure both increases and decreases in specific tyrosine kinase activity at both a whole cell/cell population level and at specific subcellular locations;
3) Ready adaptability to high throughput screening (HTS) applications and
4) Enables simultaneous monitoring of activities of more than one tyrosine kinase in real time.

The following definitions are provided to facilitate an understanding of the present invention.

The phrase "tyrosine kinase (TK) activity" means not only the enzyme activity to phosphorylate a tyrosine residue, but also the activity of the SH2 domain of the tyrosine kinase to recognize a phosphorylated tyrosine residue of other proteins and bind to the residue, and the activity of the SH3 domain of the tyrosine kinase to recognize the amino acid sequence of a proline-rich region of other proteins and bind to the region.

"Target cell" refers to any cell which expresses a tyrosine kinase, and which further contains a substrate which can be phosphorylated as a result of signal transduction. The tyrosine kinase or phosphatase may be naturally expressed by the target cell or engineered into the target cell using recombinant DNA techniques well known in the art.

A "test substance or agent" is a chemically defined compound or mixture of compounds (as in the case of a natural extract or tissue culture supernatant) whose effect on the phosphorylation by the tyrosine kinase(s) of a target cell is determined by the assay of the invention.

A "substrate" is a protein which is acted on by tyrosine kinase such that it is either phosphorylated on tyrosine residues. Tyrosine kinases can act as both a phosphorylating enzyme and a substrate.

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

A "carrier" refers to, for example, a diluent, adjuvant, excipient, auxiliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "replicon" is any genetic element, for example, a plasmid, cosmid, bacmid, plastid, phage or virus, which is capable of replication largely under its own control. A replicon may be either RNA or DNA and may be single or double stranded. Generally, a "viral replicon" is a replicon which contains the complete genome of the virus. A "sub-genomic replicon" refers to a viral replicon that contains something less than the full viral genome, but is still capable of replicating itself. For example, a sub-genomic replicon may contain most of the genes encoding for the non-structural proteins of the virus, but not most of the genes encoding for the structural proteins.

A "expression vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The terms "transfected" and "transfection" as used herein refer to methods of delivering exogenous DNA into a cell. These methods involve a variety of techniques, such as treating cells with high concentrations of salt, an electric field, liposomes, polycationic micelles, or detergent, to render a host cell outer membrane or wall permeable to nucleic acid molecules of interest. These specified methods are not limiting and the invention relates to any transformation technique well known to a person of ordinary skill in the art.

Methods of Using Nucleic Acids Encoding the Indicator Constructs of the Invention in Cellular Assays for Identification of Agents which Modulate Tyrosine Kinase Activity The methods described herein include methods (also referred to herein as "screening assays") for identifying compounds that specifically modulate (i.e., increase or decrease) tyrosine kinase activity in target cells. Such compounds include, e.g., polypeptides, peptides, antibodies, peptidomimetics, peptoids, small inorganic molecules, small non-nucleic acid organic molecules, nucleic acids (e.g., anti-sense nucleic acids, siRNA, oligonucleotides, synthetic oligonucleotides), carbohydrates, or other agents that exhibit the capacity to specifically alter tyrosine kinase function. Compounds thus identified can be used to modulate the expression or activity of these proteins in a therapeutic protocol.

Compounds to be screened or identified using any of the methods described herein can include various chemical classes, though typically small organic molecules having a molecular weight in the range of 50 to 2,500 daltons. These compounds can comprise functional groups necessary for structural interaction with proteins (e.g., hydrogen bonding), and typically include at least an amine, carbonyl, hydroxyl, or carboxyl group, and preferably at least two of the functional chemical groups. These compounds often comprise cyclical carbon or heterocyclic structures and/or aromatic or polyaromatic structures (e.g., purine core) substituted with one or more of the above functional groups.

Compounds can be identified from a number of potential sources, including: chemical libraries, natural product libraries, and combinatorial libraries comprised of random peptides, oligonucleotides, or organic molecules. Chemical libraries consist of diverse chemical structures, some of which are analogs of known compounds or analogs or compounds that have been identified as "hits" or "leads" in other drug discovery screens, while others are derived from natural products, and still others arise from non-directed synthetic organic chemistry. Natural product libraries re collections of microorganisms, animals, plants, or marine organisms which are used to create mixtures for screening by: (1) fermentation and extraction of broths from soil, plant or marine microorganisms, or (2) extraction of plants or marine organisms. Natural product libraries include polypeptides, non-ribosomal peptides, and variants (non-naturally occurring) thereof. For a review, see Science 282:63-68 (1998). Combinatorial libraries are composed or large numbers of peptides, oligonucleotides, or organic compounds as a mixture. These libraries are relatively easy to prepare by traditional automated synthesis methods, PCR, cloning, or proprietary synthetic methods. Of particular interest are non-peptide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, Curr. Opin. Biotechnol. 8:701-707 (1997). Identification of test compounds through the use of the various libraries herein permits subsequent modification of the test compound "hit" or "lead" to optimize the capacity of the "hit" or "lead" to prevent or suppress aberrant tyrosine kinase function.

In a preferred embodiment, a cell-based assay is employed in which cells expressing the indicator constructs of the invention are contacted with a test compound. The ability of the test compound to specifically modulate tyrosine kinase activity as a function of cellular fluorescence is then determined.

Kits and Articles of Manufacture

Any of the aforementioned products can be incorporated into a kit which can contain nucleic acids encoding the indicator constructs of the invention, PCR primers and other suitable reagents can be designed using the sequence information provided herein to generate indicator constructs for the specific tyrosine kinase of interest. Such kits can optionally include transfection reagents, microtiter plates for high throughput screening and cells and reagents suitable for conducting the tyrosine kinase assays described herein.

The following materials and methods are provided to facilitate the practice of the present invention. They are not intended to limit the invention in any way.

Generation of the GPhos Indicator Core:

The indicator core consists of two elements fused to a circularly permuted fluorescent molecule similar to GCAMP (Nakai, et al., 2000). The first element is the site that the targeted kinase phosphorylates on the reporter. These sites are listed in Table 1. We use consensus sites known to be selectively phosphorylated by the specific kinases of interest and recognized by a specific SH2 domain. Typically, these are sites found on the kinase of interest and known to undergo autophosphorylation. For GPhosEphB and GPhosEphA the sites used were from the juxamembrane tyrosine phosphorylation domain of the receptor tyrosine kinases EphB2 (AA573-582) and EphA4 (AA596-605), respectively. The amino acid sequence used for the GPhosEphB indicator was gsYIDPFTYEDPagle (SEQ ID NO: 1). This was encoded by the forward and reverse primers; 5'-ggatccTATATAGAC-CCTTTC ACCTATGAAGATCCTgccggcctcgag-3' (SEQ ID NO: 2) and 3'-ctcgaggccggcAGG ATCTTCATAGGT-GAAAGGGTCTATATAggatcc-5' (SEQ ID NO: 3) respectively (Upper case indicates sequence from the targeted protein and lower case indicates material added for cloning purposes. Forward primer indicated before reverse primer). For the GPhosEphA indicator the amino acid sequence used was gsYVDPFTYEDPagle (SEQ ID NO: 4). This was encoded by the primers 5'-ggatccTATGTGGATCCCTTTA-CATACGAAGACC CCgccggcctcgag-3' (SEQ ID NO: 5) and 3'-ctcgaggccggcGGGGTCTTCGTATGTAAA GGGATC-CACATAggatcc-5' (SEQ ID NO: 6). For the GPhosFyn indicator the amino acid sequence used was gsYT-DLVGEIYEDLmgle (SEQ ID NO: 7) (Brunati, et al., 1995), encoded by the primer sequences 5'-ggatccTACACTGAC-CTGGTTGGTGAAATCTA CGAAGACTTGatgggcctcgag-3' (SE) ID NO: 8) and 3'-ctcgaggcccatCAAGTCTTCGT AGATTTCACCAACCAGGTCAGTGTAggatcc-5' (SEQ ID NO: 9). For the GphosTrkB indicators the amino acid sequence used was gselgaPNYPEVLYEDWTTgale (SEQ ID NO: 10). This was encoded by the primers 5'-ggatccgagctcg-gtgctCCAAATTACCCTGAA GTCCTCTATGAAGACTG-GACCACGggtgctctcgag-3' (SEQ ID NO: 11) and 3'-ctc-gagagcaccCGTGGTCCAGTCTTCATAGAGGACTTCAG-GGTAATTTGGagcaccgagctc ggatcc-5' (SEQ ID NO: 12). For the GPhosFAK indicator the amino acid sequence used was gselgaDDYAEIIDEEDTYTMPSTgale (SEQ ID NO: 13). This was encoded by the primers 5'-ggatccgagctcggtgct-GATGACTATGCAGAGATCATCGATGAGGAAGAC-ACAT ACACCATGCCCTCGACC ggtgctctcgag-3' SEQ ID NO: 14) and 3'-ctcgagagcaccGGT CGAGGGCATGGTG-TATGTGTCTTCCTCATCGATGATCTCTGCATAGT-CATCagcaccg agctcggatcc-5' (SEQ ID NO: 15). For the GPhosMusk indicator the amino acid used was gsDRLHPNPMYQRLGNNIEYVRD1e (SEQ ID NO: 16). This was encoded by the primers 5' ggatccGACAGACT-TCATCCCAACCCCATGTACCAGCGACTGGGGA-AACAAC ATTGAATATGTCCGTGATctcgag-3' (SEQ ID NO: 17) and 3'-ctcgagATCACG GACATATTCAATGT-TGTTTCCCCAGTCGCTGGTACATGGGGTTGGGAT-GAAGTCT GTCggatcc-5' (SEQ ID NO: 18). The sequenced used for GPhosMuSK is based on the Danio rerio MuSK sequence provide to us by Dr. Michael Granato.

Figure 1C:
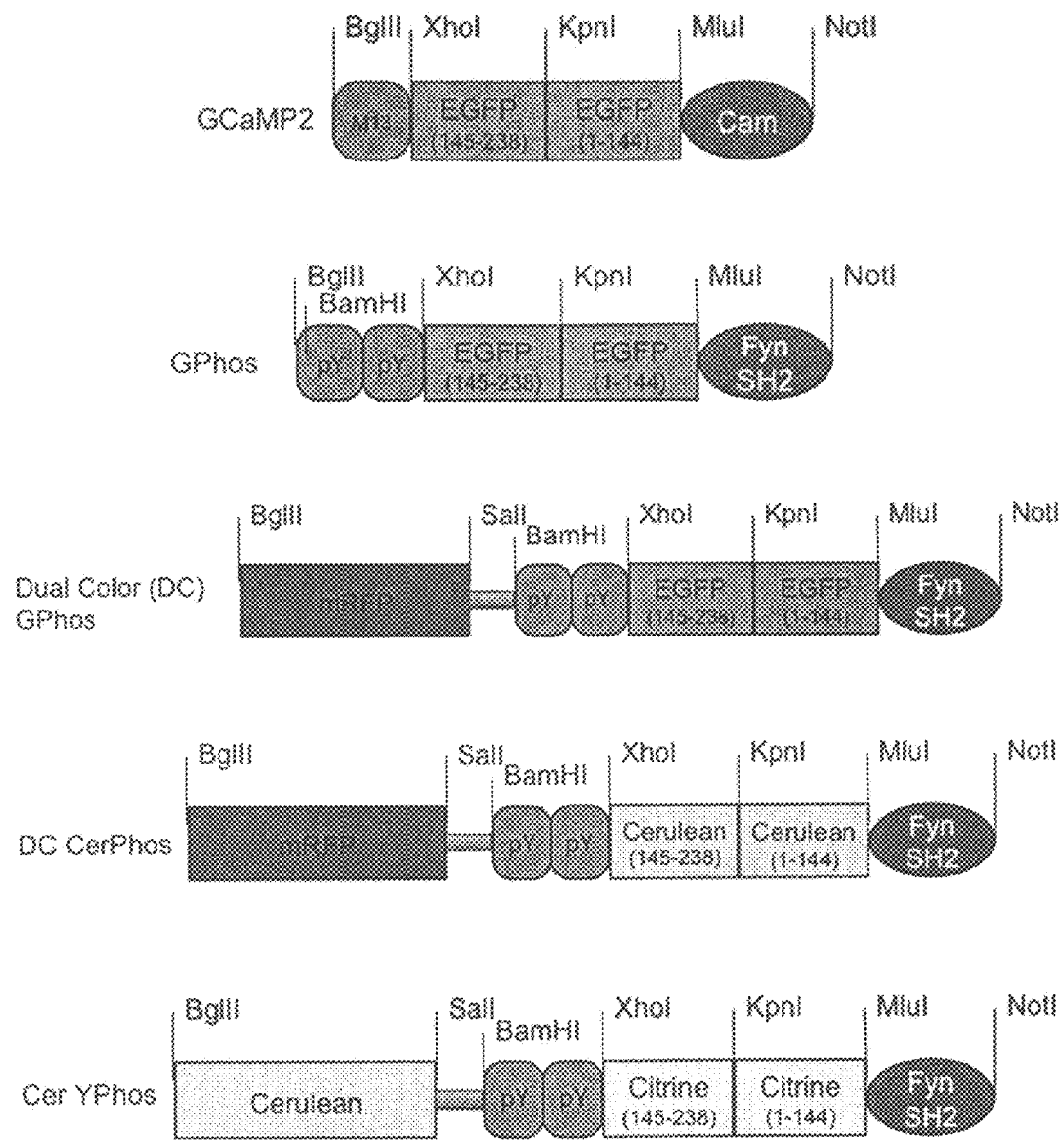

Generation of the GPhos constructs was accomplished by annealing the appropriate forward and reverse primers yielding DNA fragments with overhangs for insertion into BglII and XhoI sites. In addition, a unique BamH1 was added to each primer to facilitate future cloning and enable rapid validation of appropriate insert integration. After phosphorylation, DNA fragments were cloned using standard techniques into the BglII and XhoI sites (see FIG. 1C). Notably this approach enables us to easily change the phosphorylation sites found on the indicator. The second element of the GPhos indicator is the domain that selectively binds the phosphorylated tyrosines. For the initially indicators, we used a region containing the SH2 domain of the tyrosine kinase Fyn or Shc. We first generated primers to amplify a region from amino acid 131 to amino acid 255 of the mouse Fyn kinase. This region contains the SH2 domain as well as an additional 17 amino acids in the N-terminal and 12 amino acids in the C-terminal. For the Shc SH2 domain in the GPhosTrkB V2, we generated primers to the human Shc1 isoform 4 SH2 domain from amino acid 301 to amino acid 451. This was the minimal domain that gave us an indicator able to report changes in phosphorylation suggesting that these additional amino acids play a role in the ability of SH2 domains to bind phospho-tyrosines. N-terminal primers contained an Mlu1 site while C-terminal primers had a Not1 site to enable cloning into the vector. Again, to facilitate future cloning and enable rapid validation of insert integration, we added an AgeI site before the NotI site in the C-terminal primer (FIG. 1C). The forward and reverse primers used were respectively: 5'acgcgtGGTTACATTCCCAGCAATTACG (SEQ ID NO: 19) and TTGTACCCCACAAACTTCTGGAGGaccg-gtgcggccgc-3' (SEQ ID NO: 20).

Generation of the Dual Color Indicator:

After generating the indicator core molecule, we sought to generate a dual color molecule for that did not undergo FRET by separating the two colors with long stiff linker. To produced our ratiometric dual color indicator we fused mRFP to the indictor core with a rigid linker. To generate the rigid linker we used a DNA fragment coding for 6-alpha helical turns and added this to the N-terminus of GPhos core. The amino acid sequence used to generate the rigid linker was LAEAAA KEAAA KEAAA KEAAA KEAAA KAAA (SEQ ID NO: 21) (Arai et al., 2004). Forward and reverse primers were designed with 5' BglII and 3' BamHI overhangs, annealed together, then cloned into the GPhos vector via the BglII and BamHI sites. A unique SalI site was added at the 5' end after the BglII site to enable cloning of the fluorescent molecule. The primer sequences were 5' gatctgtc-gacTTAGCTGA AGCTGCTGCTAAAGAAGCTGCT-GCTAAAGAAGCTGCTGCTAAAGAAGCTGCTGC TAAAGAAGCTGCTGCTAAAGCTGCTGCTg 3' (SEQ ID NO: 22) and 5' gatccAGCAGCAGCTTTAGCAGCAGCT-TCTTTAGCAGCAGCTTCTTTAGCAGCAGCT TCTT-TAGCAGCAGCTTCTTTAGCAGCAGCT-TCAGCTAAgtcgaca 3' (SEQ ID NO: 23) for the forward and reverse primers respectively.

We chose mRFP to generate the dual color indicator as it can be easily optically separated from the GPhos signal and has a similar bleaching rate to GFP. The primers to amplify full-length mRFP contained a 5' BglII and 3' SalI site. After PCR, the fragment was ligated to the construct containing the 6-helical turn linker domain fused to the GPhos core via BglII and SalI sites. The primers for mRFP are 5'-agatct-gatctgccgccaccATGG CCTCCTCCGAGGACG (SEQ ID NO: 24) and CTCCACCGGCGCCgtcgac-3' (SEQ ID NO: 25).

Generation of Other Circularly Permuted Permutated Fluorescent Proteins:

The CFP/YFP versions of the indicator were made by circularly permutating either Cerulean (CFP) or Citrine (YFP) (from D. Piston and R. Tsien labs, respectively) similarly to the protocol described for GCaMP2 (Tallini et al., 2006). Since both Cerulean and Citrine are homologus, the same primers were used to make circularly permuted (cp) Citrine and cpCerulean. The primers for cloning the N-terminal portion of the cp proteins (AA145-240) are 5'-ctcgagAACGCCATCAGCGACAACG (SEQ ID NO: 26) and 5'-ctcgagGGTGGATACAACAGCCA-CAACGTCTATATCATGG (SEQ ID NO: 27) for the cerulean and citrine forward primers respectively and GCATG-GACGAGCTGTACAAGggcggtacc-3' (SEQ ID NO: 28) for the reverse primer. The forward primer contains a 5' XhoI site and the reverse primer contains two glycines and a KpnI site at the 3' end. The primers for cloning the C-terminal portion (AA1-144) of the cp protiens are 5'-ggtaccGGAGG-GAGCGTGAGCAAGGGCGAGGAGC (SEQ ID NO: 29) and GGGGCACAAGCTGGAGTACAACGGTggaacgcgt-3' (SEQ ID NO: 30) for the forward and reverse primers respectively. The forward primer contains a 5' KpnI site and the reverse primer contains two glycines and a MluI site at the 3' end. The single point mutations were made by QuickChange (Stratagene) using the following primers (forward primer shown only); V163A: 5'-GCATCAAGGCGAACTTCAA-GATCC-3' (SEQ ID NO: 31), S175G: 5'-GGACGGCG-GCGTGC-3' (SEQ ID NO: 32), D180Y: 5'-GCTCGCCTAC-CACTACC-3' SOE ID NO: 33), A206K: 5'-CCAGTCCAAGCTGAGCAAAGACC-3' (SEQ ID NO: 34), V93I: 5'-CGAAGGCTACATCCAGGAGC (SEQ ID NO: 35),-3' however for cpCerulean only the V93I and D180Y mutations were made. We named the cpCitrine core version of the indicator YPhos and the cpCerulean core version of the indicator CerPhos.

Subcellular Targeting

Specific tyrosine phosphorylation signaling that underlies relevant biological events usually occurs in different subcellular domains and compartments such as dendritic spines, cell membranes or within the nucleus. While our cell-filling indicators can effectively report signals from fine structures, it would be advantageous to enrich our indicators in structures of interest. To do this we have begun to develop indicators that are specifically targeted to particular subcellular microdomains. To target our indicator to specific cellular domains we have developed a myristylated GPhosfyn that is enriched in the cell membrane. In these GPhos indicators, we fused the myristylation signal from src kinase (GSSKSKP-KDPSQRRR) (SEQ ID NO: 36) to the N-terminus of GPhos and introduced a glycine-rich linker domain [(GGGGS)$_{3-4}$] (SEQ ID NOs: 37 and 38) that separates the GPhos molecule from the myristalation signal in order to provide a break in secondary structure. Other targeting sequences that can be employed include, without limitation, a Gphos-PDZ with a PDZ binding domain to localize the indicator to synaptic sites, a GPhos-NUC with a nuclear localization signal, a Gphos-PAL with a palmitylation signal and a Gphos-Export with a nuclear export signal. The skilled artisan is familiar with such targeting sequences and the do not need to be listed here.

Generation of the Dual Color Cerulean/Citrine Indicator:

The dual color Cerulean/Citrine indicator was generated by first replacing the cpGFP in GPhos with the cpCitrine from YPhos via the XhoI and MluI sites (FIG. 1C). Next, full length Cerulean was cloned into the dual color mRFP/YPhos construct via the BglII and SalI sites thus replacing mRFP. In addition, an EcoRV site was added after the 5' BglII site to allow for insertion validation. The primers used for the full length Cerulean PCR were 5'-agatctgatatcgccgccaccATGGT-GAGCAAGGGCGAGGAG (SEQ ID NO: 39) and GGCATGGACGAGCTGTACAAGgtcgac-3' (SEQ ID NO: 40) (forward and reverse respectively).

HEK 293T Cell Culture:

HEK 293T cells were grown in 293T cell media (DMEM (Invitrogen), 10% FBS (Hyclone), Pen/Strep, and glutamine (both from Invitrogen) in a humidified 37° C., 5% CO$_2$ incubator. Cells were plated on poly-d-lysine and laminin (both from BD biosciences) coated glass cover slips (12 mm, #1 German glass; Bellco Glass) in 24-well microplates (Corning) for imaging or in 6-well tissue culture plates (Corning) for immunoprecipitation. Cells were transfected using the calcium phosphate precipitation method (Xia et al., 1996) with 4.5 mg of GPhos indicator DNA, and 0.25 mg of Eph receptor DNA or 1 mg of PDGFR (all from Dalva Lab) per well of a 6-well plate or 4 wells of a 24-well plate. Transfected cells were imaged or lysed 24-48 hours after transfection.

HEK293T Immunoprecipitation:

Cells were treated with 3 mM PP2, 100 nM TPA, preclustered EphrinB2-FC or EphrinA1-FC (both at 500 ng/ml, R&D Systems) for 30 minutes before being lysed in 0.5 ml of TBS-V lysis buffer (20 mM Tris-base, pH 7.5, 140 mM NaCl, 10 mM NaF, 1 mM Na$_3$VO$_4$, 1 mM EDTA) containing, PMSF, DTT, Protease Inhibitor Cocktail (Sigma), Phosphotase Inhibitor Cocktail 2 and 3 (Sigma) and 0.25% vol/vol Nonidet P-40 detergent (NP-20, Pierce). Cell debris was removed by centrifugation at 14,000×g for 30 minutes at 4° C. Ten percent of lysate was saved as input control. Remaining lysate was incubated with 1 ml of rabbit anti-GFP (Invitrogen) overnight at 4° C. with protein G agarose beads (Invitrogen). Immunoprecipitated beads were then washed 3× with TBS-V lysis buffer containing protease inhibitors, DTT, PMSF and detergent (NP-40) then an additional three times with TBS-V before resuspension in Laemelli sample buffer (Biorad). The immunoprecipitated proteins were boiled for 10 minutes then run on a 10% SDS-PAGE gel. Proteins were transferred to a 0.45 mm PVDF membrane (Millipore) and probed for phosphorylated tyrosines using mouse anti-Py99 (1:100: SantaCruz) and rabbit anti-GFP as a loading control (1:2500; Invitrogen). Immunoblots were blocked with 5% milk in TBST (150 mM NaCl, 10 mM Tris pH 8.0, 0.05% Tween 20).

HEK 293T Cell Specificity:

For the indicator specificity experiments, HEK cells were imaged in artificial cortical spinal fluid (ACSF; 140 mM NaCl, 5 mM KCl, 1 mM MgCl$_2$, 2 mM CaCl$_2$, 20 mM glucose, and 10 mM HEPES, pH 7.2) at room temperature on a laser scanning confocal (Leica). Images were taken as 3-4 mm z-projections (0.7 mm step size) every three minutes. After a 15 minute baseline, either 20 ng/ml of PDGF (Invitrogen), or 500 ng/ml of DyLight 649 (Jackson Immunoresearch) labeled pre-clustered EphrinB2-FC or EphrinA1-FC was added and imaged for 30 minutes. Images were analyzed via the NIH ImageJ program as detailed below.

EphB2 and EphA4 Kinetics Imaging:

Cells were imaged in ACSF on a spinning disk confocal (PerkinElmer) encased in a humidified temperature controlled incubator attached to a CCD-EM camera (Hamamatsu). Images were taken as a 3-4 mm z-projection (1 mm step size) every 20 seconds. After a 2 minute baseline, cells were treated and imaged with either DyLight 649 (Jackson Immunoresearch) labeled EphrinB2-FC or DyLight 649 labeled EphrinA1-FC (both at 500 ng/ml) for 15 minutes. Before continuing the experiment, bath was exchanged with fresh ASCF. Genistien (10 μm; Calbiochem) was added to previously imaged cells after a 2 minute baseline and imaged for an additional 15 minutes. Images were collected via Volocity software and analyzed using NIH ImageJ as detailed below.

Neuronal Cell Culture and Imagining:

Primary cortical neurons were isolated from embryonic day 17-18 rats and cultured in Neurobasal media supplemented with B27, pen/strep, and glutamine (all from Invitrogen). Cells were plated onto poly-d-lysine and laminin coated glass coverslips in 24-well plates at a density of 125 k/well. At 4 days in vitro (DIV) cells were transfected with 1 ml Lipofectamine 2000 (Invitrogen) per coverslip, 1.5 mg of pTre GPhosEphB and 1.5 mg pTet-On per 4 coverslips. Neurons were imaged at 6-9 DIV in ACSF at 37° C. on a spinning disk confocal encased in a temperature and humidity controlled incubator and attached to a CCD-EM camera. Images were taken every 30 seconds at 0.5 mm sections for 3-4 mm. DyLight 649 labeled pre-clustered EprhinB2-FC was added after a 30 minute baseline for 1 hour. Data was collected using the Volocity program and analyzed via the NIH ImageJ program as detailed below.

Image Analysis:

Image analysis was conducted off-line using NIH ImageJ using both custom and standard macros. Images where first smoothed using a standard Gaussian (radius=1 pixel). To calculate the ratio change, we used the GPhosRatio macro to measure the average non-zero value for the area selected. Ratio change was calculated as $DF/F=(F-F_0)/F_0$ (Yuste and Konnerth, 2005). Significance between conditions was determined by two-way ANOVA with Bonferroni post-hoc tests. Receptor "on" kinetics were calculated as one-phase association, and "off" kinetics were calculated as one-phase decay. All statistical measures were conducted using GraphPad Prism version 5.00 (GraphPad Software, San Diego, Calif.) on a per coverslip basis with several cells analyzed per coverslip from a minimum of three independent experiments.

For images collected using our laser-scanning confocal, the ratio images were made using the RatioPlus macro. The background was measured as the average signal of a region with no transected cells of approximate 50×50 pixels. The "clipping value" was determined based on imaging parameters specific to each system (see: rsbweb.nih.gov/ij/plugins/ratio-plus.html). Non-integer values were set to zero using the ScaleRatio macro.

For images collected using our spinning disk confocal, the "image calculator" function in ImageJ was used to generate a 32-bit ratio image (GPhos image/mRFP image). Areas outside of the imaged cells were set to zero by subtracting a binary mask of the transfected cells created from the sum of the Gphos and mRFP images. The resulting images quantified by measuring average ratio values using standard ImageJ tools.

The Examples set forth below are provided to illustrate certain embodiments of the present invention. They are not intended to limit the invention in any way.

Example I

Dual Colored Ratiometric Fluorescent Indicators of Tyrosine Kinas Activity

To begin to probe the dynamics of TK signaling, novel genetically encoded fluorescent phosphorylation reporters (Phos) have been developed that allow for visualization and quantification of both increases and decreases in TK signaling within specific subcellular domains of neurons.

We have focused on understanding the dynamics of tyrosine phosphorylation for several reasons. First, tyrosine phosphorylation is a prominent mechanism by which cells modify protein function in response to environmental cues. Second, work from a number of investigators indicates that tyrosine kinase signaling is critical for formation of dendritic spines, synapses, and for synaptic plasticity (Irie and Yamaguchi, 2004). Finally, detailed information is available about substrate sequence requirements and binding specificities of phospho-tyrosine interacting SH2 domains (Pawson, 2004). For instance, the SH2 domain on the src family tyrosine kinase recognizes a phosphorylated tyrosine (pY) with a consensus sequence of pYEEI (SEQ ID NO: 41), while the SH2 domain on PLC-g recognizes pYXXM (SEQ ID NO: 42) (Songyang et al., 1993). Importantly, as additional information is generated regarding protein interaction domains, our approach will be adaptable for visualization of other types of signaling pathways.

Genetically encoded indicators provide tools to define spatiotemporal dynamics of signaling events in the context of living cells. To date, a number of different platforms using genetically encoded indicators have been developed that report the activity of specific signaling events. While fluorescent indicators that monitor activity of second messengers such as calcium (Miyawaki et al., 1997; Pologruto et al., 2004), inositol 1,4,5-triphosphate (Hirose et al., 1999), DAG (Oancea et al., 1998), cAMP (Zaccolo et al., 2000) and cGMP (Honda et al., 2001) have been developed and visualized in living cells, development of genetically encoded indicators that monitor kinase signaling has lagged behind. In work funded in part by the Dana Foundation, investigators have generated fusion proteins consisting of a fluorescent protein, such as GFP, fused to an SH2 domain. The GFP protein is then recruited to the appropriate phosphorylated-tyrosine reside. Clusters of phosphorylated proteins can then be visualized as puncta of GFP (Robles et al., 2005; Robles and Gomez, 2006). Remarkably, these fusion proteins appear not to affect cell function and have been used extensively to examine where there are clusters of phosphotyrosine reside within live axonal growth cones. This approach has proven fruitful, and can provide detailed information about where signaling molecules may be localized. However, GFP-SH2 domain fusion proteins appear to recognize all suitable substrates rather than reporting on the activity of specific types of kinases. Thus, while these reporters show where within a cell tyrosines are phosphorylated, the indicators described herein enable analysis of activity and kinetics from specific tyrosine kinase enzymes.

Figure 2:
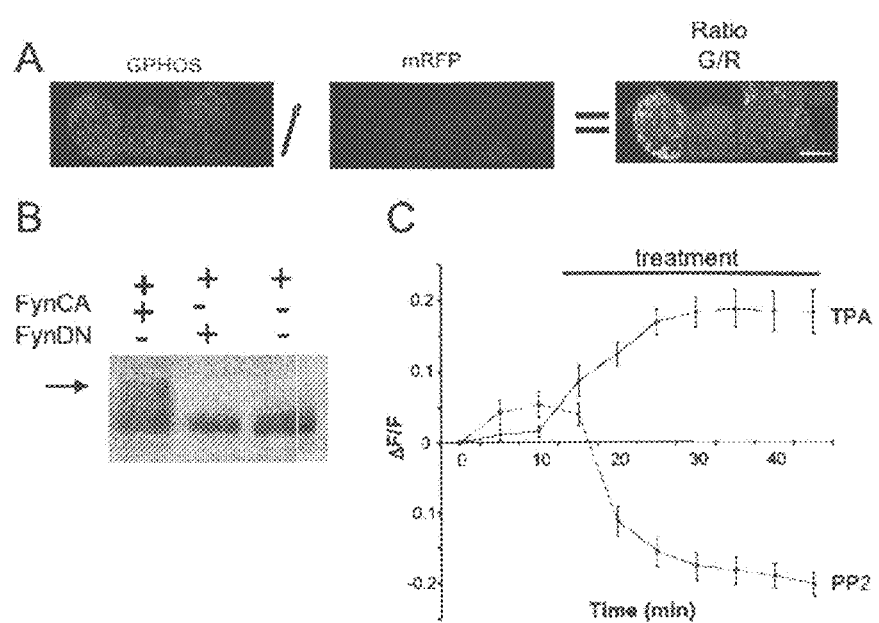
FIG. 2: GPhos indicator can report increases and decreases in RTK activity. A) Cells transfected with GPhos, mRFP and a constitutively active form of fyn tyrosine kinase (FynCA). Ratiometric images were generated by dividing the green GPhos image by the red cell filling image on a pixel-by-pixel basis. B) Western blot analysis of HEK 293T cells transfected with GPhos, mRFP, FynCA. Co-transfection with FynCA revealed a larger apparent molecular weight band indicative of phosphorylation not present in cells co-transfected with a dominant negative form of fyn (FynDN). C) Graph showing the fluorescence change in cells by either activating tyrosine phosphorylation with a phorbol-ester (100 nm, TPA) or inhibiting src tyrosine kinase dependent phosphorylation (3 µm, PP2). Bar indicates drug application.
Figure 3:
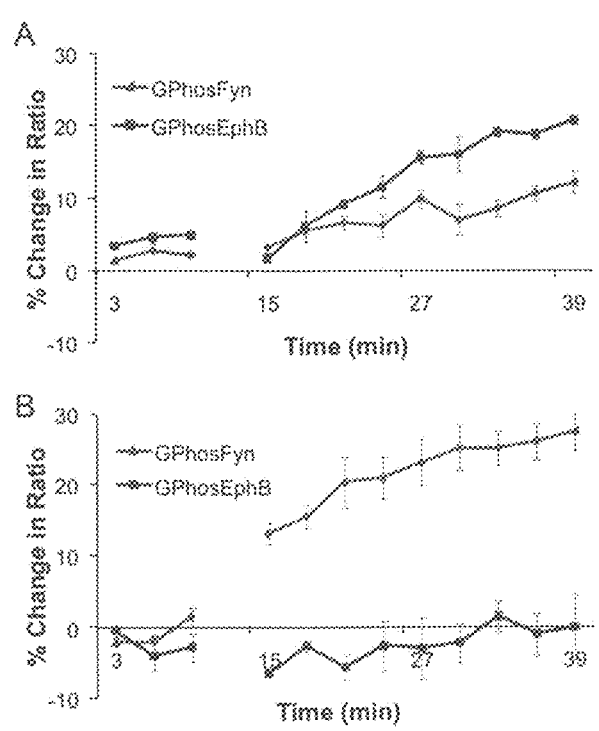
FIG. 3: Specificity of GPhos indicators. A) Responses of HEK293T cells transfected with EphB2 and treated with activated ephrinB2-fc. As expected, both GphosEphB and GPhosfyn indicators report increases in phosphorylation. B) Responses of HEK293T cells transfected with EphA4 and treated with activated ephrinA1-fc. As expected only Gphosfyn reports increased phosphorylated.
Figure 4:
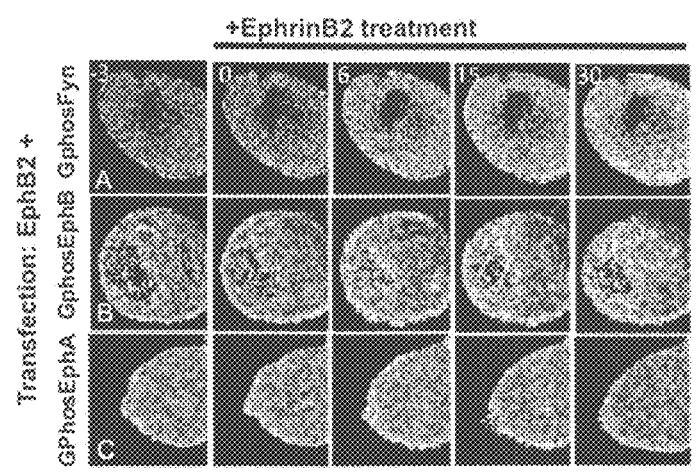
FIG. 4: Specificity of GPhos Indicators. Examples the response to ephrin-B2 treatment of HEK293T cells transfected with three different dual color phos indicators and EphB2. A) Cells transfected with GPhosFyn. Response appears to be principly in cell body. B) Cells transfected with GPhosEphB. Response appears first at membrane of cell. C) Cells transfected with GPhosEphA. Cells shown no response. Images were collected every three minutes.
Figure 5:
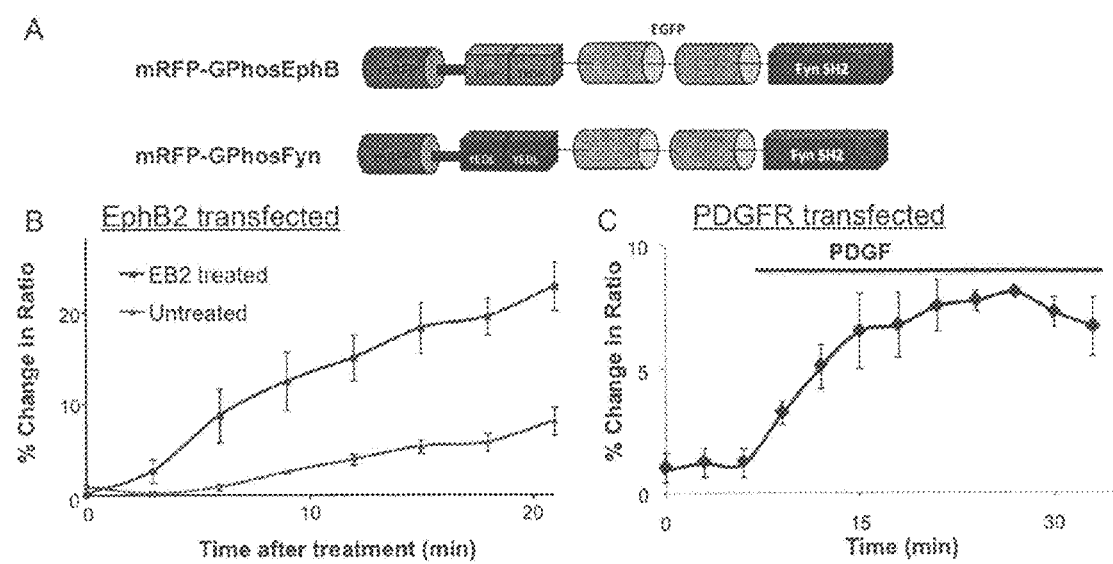
FIG. 5: Dual color Phos indicators: A) Schematic diagram of two types of dual color indicators with mRFP fused to GPhosEphB and Gphosfyn via a rigid linker to prevent FRET. YEDL (SEQ ID NO: 87), YIDP (SEQ ID NO: 88), and YEDP (SEQ ID NO: 89) are shown. B) Quantification of change in ratio of mRFP-GphosEphB in HEK293T cells transfected with EphB2 and stimulated with activated ephrinB2-fc or control. C) Quantification of change in ratio of mRFP-Gphosfyn in HEK293T cells transfected with the PDGFR and stimulated with PDGF.
Figure 6:
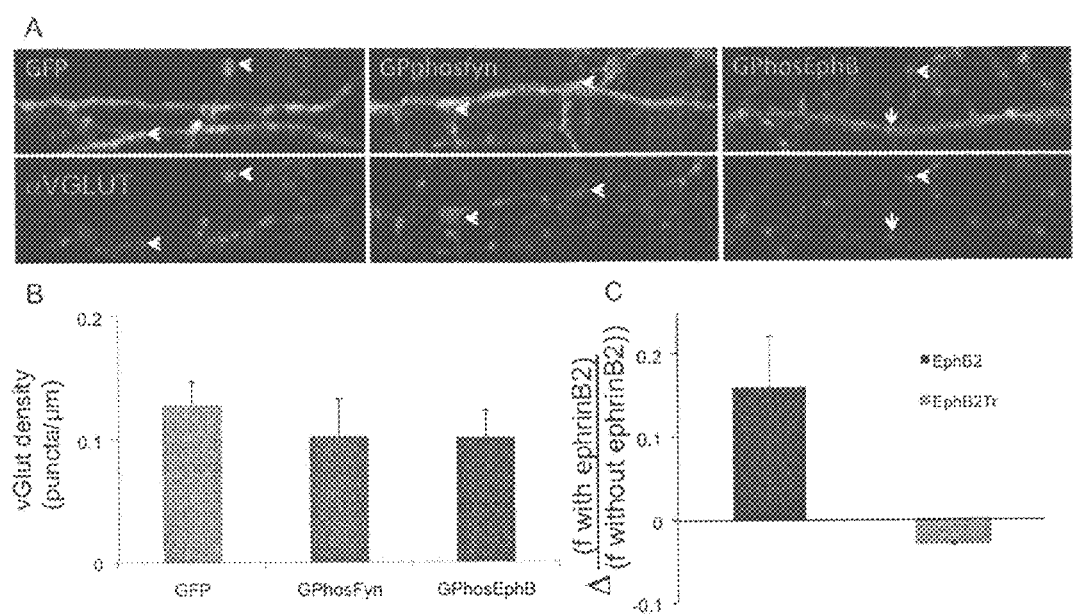
FIG. 6: Gphos validation in neurons. A) Representative images of neurons transfected with control, Gphosfyn, or GphosEphB and mRFP. Neurons were fixed and stained with anti-VGlut antibodies to mark excitatory presynaptic terminals (bottom panels). Arrows indicate examples of vGlut puncta that co-localize with transfected neurons. B) Quantification of vGlut puncta density. There is no significant difference between the three groups. C) Quantification of the change in GphosEphB signaling in areas of neurons transfected with wild-type or dominant negative EphB2 (EphB2 and EphB2Tr) contacting CY5 labeled particles of activated ephrinB2-fc. Blocking EphB signaling prevents the response of our indicator to ephrinB2-fc.
Figure 8:
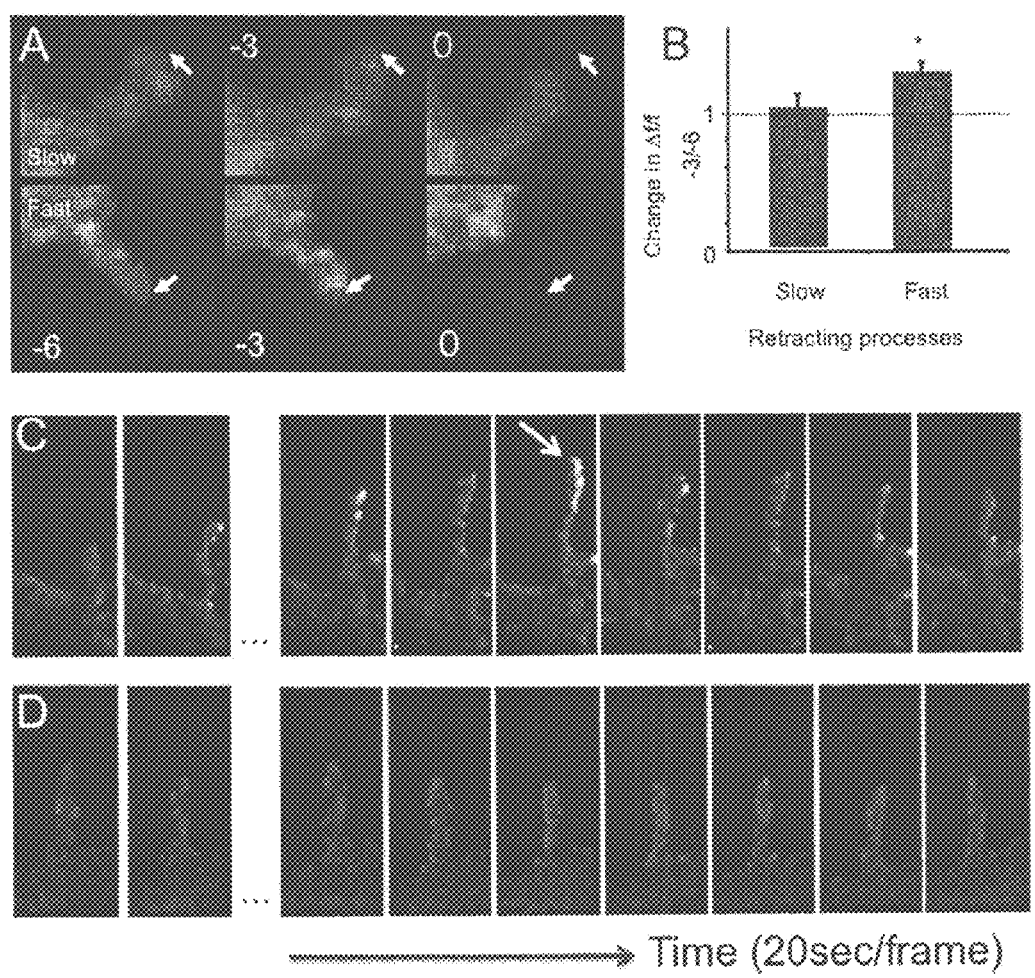
FIG. 8: Dynamic EphB signaling in motile dendritic filopodia. A) Images of two filopodia (Slow, top; Fast, bottom) from neurons transfected with GphosEphB. Images are collected every three minutes. Arrows indicate maximum extension of the filopodia. B) Quantification of the change in ratio signal just prior to the start of filopodia retraction. C) Images of a filopodia from a neuron transfected with mRFP-GphosEphB. Images are collected every 20 seconds. Arrow indicate peak of Gphos signal just prior to the start of retraction. D) Images of a Stable filopodia collected as in C. GPhosEphB signaling remains stable during imaging period.
Figure 9:
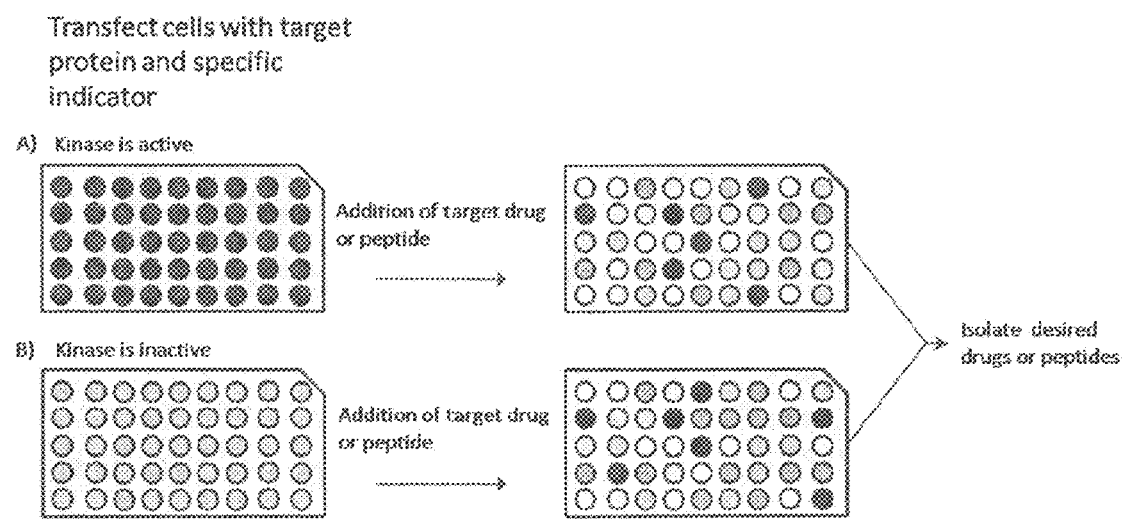
FIG. 9: GPhos indicator can also be used in HTS applications, for example to screen for peptides or drugs that block or activate specific kinases. As shown in the schematic diagram high through put screening assays can be employed to identify test substance with specifically or non-specifically modulate tyrosine kinase activity.

We have overcome many limitations of other indicator systems by developing a fluorescent phosphorylation indicator, analogous in design to the G-CAMP calcium reporters (Nakai et al., 2001; Kawai et al., 2004; Tallini et al., 2006), which enables effective signal detection and measurement of dynamic signaling events using a relatively simple imaging approach based on brightness changes. See FIGS. 1 and 2. Our system is further improved over other indicator systems by using a second color of genetically encoded fluorophore that is insensitive to changes in phosphorylation to visualize cell morphology and control for changes in cell shape. See FIGS. 1, and 4, and 5. Using this dual-color ratiometric indicator system, we can measure ratiometric changes in phosphorylation-induced fluorescence, which enables us to visualize and quantify the amount of tyrosine phosphorylation in living cells.

We have made a number of single color and two color fluorescent indicators of phosphorylation. We call the indicator portion of these tools GPhos (Green fluorescent phosphorylation indicator), YPhos (Yellow fluorescent phosphorylation indicator) and CPhos (Cerulean fluorescent phosphorylation indicator (FIG. 1). Each XPhos molecule is based on a core of a single, circularly permutated cyan, green, or yellow fluorescent protein (CFP, GFP or YPF respectively), flanked on the N-terminus by two consensus phosphorylation sites. For the studies described herein, we have generated and characterized Phos molecules specific for fyn, EphB, or EphA tyrosine kinases by generating molecules with two consensus phospho-tyrosines on the N-terminus (Songyang et al., 1993; Nakai et al., 2001; Kawai et al., 2004; Pawson, 2004). Phosphorylation at one or more of the consensus sites causes the SH2 domain to bind the phospho-tyrosine consensus site. This in turn changes the structure of the PHOS indicator and the fluorescence signal is increased (FIG. 1). Our initial characterization of the Phos indicators demonstrates that they can report increases and decreases in phosphorylation, respond selectively to activation of specific tyrosine kinases, do not affect synapse development, and have high spatial and temporal resolution (FIG. 2-8).

Our results demonstrate the sensitivity of the detection reagents described herein. We have 1) begun to use these tools to detect TK signaling in filopodia (FIG. 8) and developing methods for monitoring multiple signaling molecules simultaneously (FIG. 7).

We have recently found that EphB2 is required for normal motility of dendritic filopodia (Kayser et al., 2008). Therefore, we next sought to test whether our indicator would detect EphB signaling within moving dendritic filopodia. Consistent with previous reports (Ziv and Smith, 1996; Mattila and Lappalainen, 2008), many dendritic protrusions along these neurons were highly dynamic, while others were stable for the imaging period. In preliminary experiments images were collected every 20 seconds from neurons transfected with our dual color mRFP-GPhosEphB indicator. Consistent with our findings using slower time resolution imaging, rapidly retracting filopodia often have GPhosEphB signals at the tips or along the side of moving filopodia (FIG. 8C). Our preliminary findings in filopodia demonstrate that our indicator can report changes in signal reliably from fine subcellular domains. In addition, these results begin to expand our understanding of how EphB kinases regulate filopodial motility. Consistent with our published work, these results suggest that EphBs are highly active in motile filopodia, but they provide novel information about when and where EphBs acts, suggesting that EphBs signal to regulate fast retractions.

The existence of different color fluorescent proteins raises the opportunity to make different color Phos indicator proteins. In particular, CFP, GFP and YFP and their variants (Cerulean, EGFP, citrine) share similar secondary structure and differ by only a few amino acids, but have distinct emission spectra. Importantly, one can easily separate CFP and YPF making dual color labeling experiments possible. We have already developed versions of our indicator based on cerulean, EGFP, and citrine (YPhos). We have generated and tested CPhos-EphB and YPhos-fyn indicators. Lambda scans of the emission spectra of these proteins expressed in HEK293T cells reveal the expected spectra (FIG. 7B). Moreover, our data indicate that in HEK293T cells each indicator functions to report changes in phosphorylation. Additional sets of indicators based on CPhos and YPhos can also be generated. See Table I. These molecules will enable us to image the activity of different tyrosine kinases within the same neuron at the same time. The reporters described provide the ability to determine the sequence and pattern of response of a series of kinases to specific biological responses.

TABLE 1

Design of indicators for most families of RTKs (provided sequences are SEQ ID NOs: 43-86, from top to bottom)

| Receptor protein | Tyrosine position | Specific phosphorylation domain | SH2 interacting domain |
|---|---|---|---|
| Fyn | src SH2 consensus | pYTDLVGEIpYEDI | fyn, src |
| Src | Y527 | EPQpYQPGEN | src, fyn |
| Lck | Y505 | TEGQpYQPQP | fyn, src, lck |
| Lyn | Y507 | EGQpYQQQP | src, lyn |
| FAK | Y397 | TDDpYAEIID | Csk |
| FAK | Y526 | LILpYApYQLSTA | Csk |
| Cbl | Y731 | CTpYEAMYNIQ | p85 |
| Abl | Y488 | PEKVpYELMR | Abl, Src |
| EphB1 and EphB2 | Y605/Y611 | IpYIDPFTpYEDPNE | src, fyn, RasGAP, Crk, Nck |
| EphB3 | Y603/Y609 | VpYIDPFTpYEDPNE | src, fyn, RasGAP, Crk, Nck |
| EphB5 | Y610/Y616 | pYpYIDPSTpYEDPNE | scr, fyn, RasGAP, Crk, Nck |
| EphA4 | Y596/Y602 | pYVDPFTpYEDP | src, fyn |
| EphA1 | Y600/Y606 | LKpYVDLQApYEDPAQ | src, fyn |
| TrkA | Y490 | IENPQpYFSDA | Shc, FRS2 |
| TrkA | Y670/Y674/Y675 | IpYSTDpYpYRVG | Grb2, SH2B, rAPS |
| TrkA | Y785 | PPVpYLDVLG | PLC-g |
| TrkB | Y533 | IENPQpYFGI | Shc, FRS-2 |
| TrkB | Y719/Y723/Y724 | VpYSTDpYpYRVG | Grb2, SH2B, rAPS |
| TrkB | Y835 | SPVpYLDILG | PLC-g |
| TrkC | Y516 | IENPQpYFRQG | Shc |
| TrkC | Y706/Y710/Y711 | pYSTDpYpYRLFN | Grb2, SH2B, rAPS |
| TrkC | Y835 | TPIpYLDILG | PLC-g |
| ErbB1 | Y627 | NCTpYGCAGP | Gab1 |
| ErbB1 | Y317 | GPDYpYEVEED | Shc |
| ErbB1 | Y1068 | LQRpYSSDPT | Grb2 |
| ErbB2 | Y1139 | QPEpYVNQPDV | Grb7 |
| FGFR1 | Y766 | NQEpYLDLSIP | Grb14, PLC-g |
| FGFR1 | Y583/Y585 | GLEpYCpYNPS | FRS-2 |

TABLE 1-continued

Design of indicators for most families of RTKs
(provided sequences are SEQ ID NOs: 43-86,
from top to bottom)

| Receptor protein | Tyrosine position | Specific phosphorylation domain | SH2 interacting domain |
|---|---|---|---|
| FGFR1 | Y463 | VSEpYELPEDP | Crk, src, fyn |
| FGFR1 | Y556 | GPpLYVIVEYA | Grb2 |
| FGFR2 | Y671 | NEEpYLDLTQP | Grb14, PLC-g |
| FGFR2 | Y368 | VSEpYELPEDP | Crk, src, fyn |
| FGFR2 | Y463 | GPpLYVIVEYA | Grb2 |
| FGFR3 | Y724 | HDLpYMIMRE | SH2B |
| FGFR3 | Y760 | TDEpYLDLSVP | SH2B, Grb14, PLC-g |
| PDGFR | Y579/Y581 | GHEpYIpYVDPVQ | src, fyn, yes |
| PDGFR | Y857 | DSNpYISKGS | Src |
| PDGFR | Y1021 | NEGDNDpYIIPLP | PLC-g |
| PDGFR | Y751 | SIDpYVPMLD | Nck |
| PDGFR | Y684 | ITEpYCRYGDL | Grb2 |
| VEGFR-2 | Y1175 | ADPpYITPEM | Plc-γ |
| VEGFR-2 | Y1214 | KFHpYDNTA | Grb-2 |
| IRS-1 | Y895/Y1172 | PGEpYVNIEF/ SLNpYIDLDLA | Fyn |

During the past decade stunning advances have been made in imaging, molecular biology and biochemistry that have greatly advanced our understanding of neuronal plasticity and development. TK signaling underlies many developmental processes such as cell differentiation, survival, axon guidance, and synapse formation. In addition, tyrosine kinases are key regulators of plasticity. However, our understanding of how tyrosine kinases act dynamically is not well defined. Within the field of neuroscience, visualization of signaling dynamics during synaptic plasticity and development will transform our understanding of these events and provide deep insights into fundamental aspects of diseases such as addiction, cancer, and neurodegenerative disorders where tyrosine kinases activity is abnormal.

Example 2

Screening for Test Agents which Modulate Tyrosine Kinase Function

Precise activation of receptor tyrosine kinases is important for specifying the biological outcome and over-activation that can result in diseases such as cancer. Tyrosine kinases are important in many diseases and are often seen as 'drugable' targets, but rapidly testing whether candidate compounds selectively alter the function of these targets is difficult and costly. Our transfectable indicators with their high signal to noise ratio offer a powerful new way to screen for reagents that alter tyrosine kinases.

In one approach, cells can be transfected with the indicators described herein thus providing an in vivo read out of specific kinase activity. The ability of different compounds to alter this specific activity can then be monitored using standard high resolution plate reading tools. The indicators described enable detection both increases and decreases in TK signaling. Candidate compounds which induce the desired response (e.g., increase or decrease) would then be selected for further analysis. By using indicators for several different TKs, the selectivity and specificity of such compounds can be determined. With the simple time lapse imaging approaches provided in Example I, our screening system also facilitates characterization of the temporal and spatial dynamics of the effects of these candidate compounds on TK activity, thereby providing facile visualization of selectivity, specificity, and dynamics of TK signaling in real time.

Figure 10:
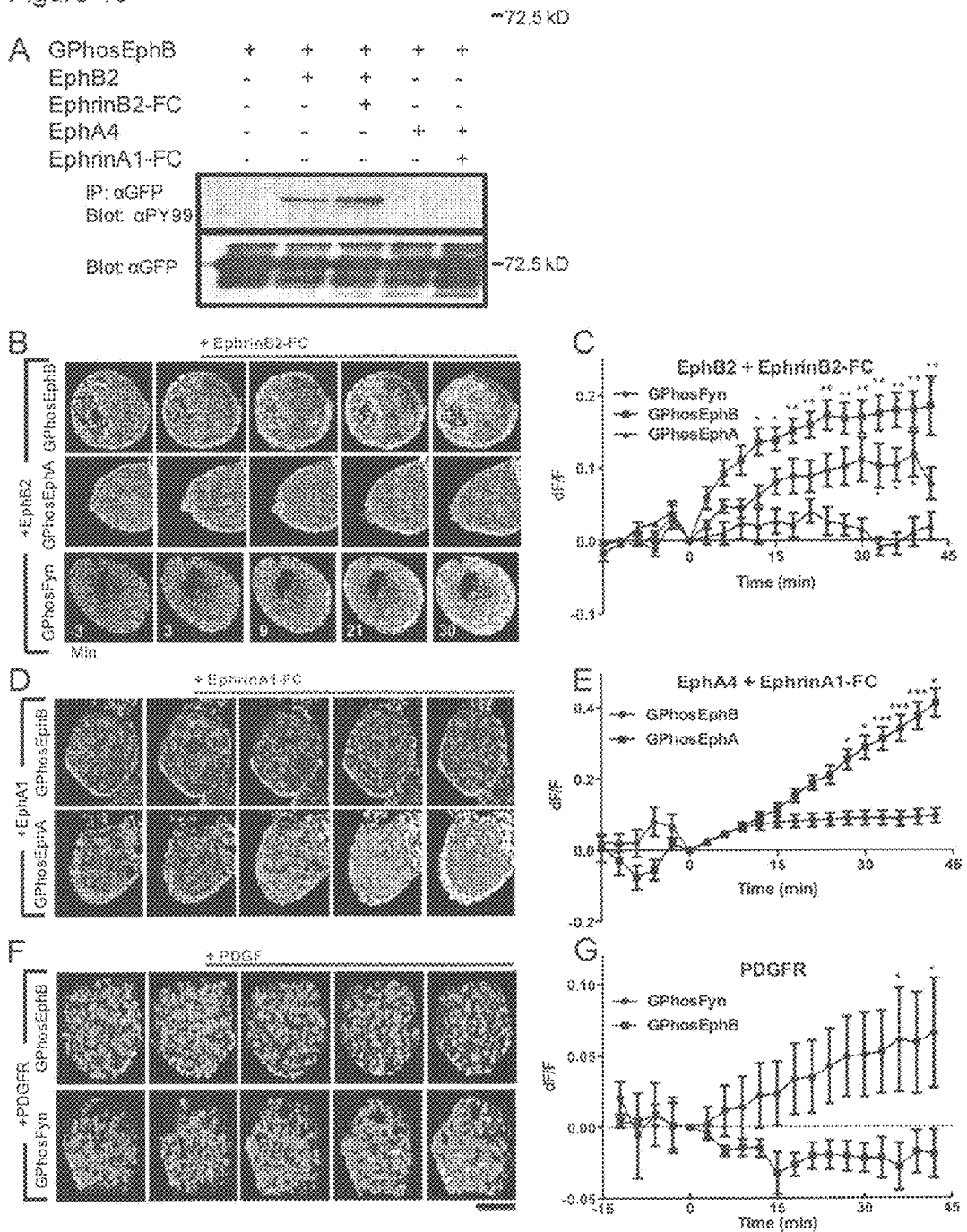
FIG. 10: Indicators report kinase activity for specific tyrosine kinases A) Representative western blot of HEK 293T cells transfected with GPhosEphB indicator and either EphB2 or EphA2, with and without 30 minutes of appropriate Ephrin treatment. Upper blot is with a phosphotyrosine antibody, lower blot is lysate control blotted αGFP. B & C) Cells transfected with EphB2 and either GPhosEphB, GPhosEphA or GPhosFyn. Images were taken every three minutes. B) Indicator response to EphrinB2-FC treatment (indicated by orange bar). C) Change in florescent ratio after EphrinB2-FC treatment. Time indicates minutes after treatment. D & E) Cells transfected with EphA4 and either GPhosEphB or GPhosEphA. Images were taken every three minutes. D) Indicator response to EphrinA1-FC treatment (indicated by orange bar). E) Change in florescent ratio after EphrinA1-FC treatment. Time indicates minutes after treatment. F & G) Cells transfected with PDGFR and either GPhosEphB, or GPhosFyn. Images were taken every three minutes. F) Indicator response to PDGF treatment (indicated by orange bar). G) Change in florescent ratio after PDGF treatment. Time indicates minutes after treatment. Scale bar, 10 µm. Error bars indicate std error of the mean (n=6(C), 2(E), 5(G)).

Our indicators respond robustly and selectively to TKs based on their SH2 and phosphorylation sites. As proof of principle, we have used specific ligands for different RTKs and found that they can give distinct and selective responses to appropriate stimuli. For instance, GphosEphB gives a robust response to ephrin-B treatment, but not ephrin-A treatment (FIG. 10). Notably, our GPhosFyn reporter responds appropriately to stimulation of a number of kinases known to activation fyn signaling. These include EphB, and the PDGFR (FIG. 10). These experiments provide a test agent for the indicators showing their ability to be activated.

Figure 11:
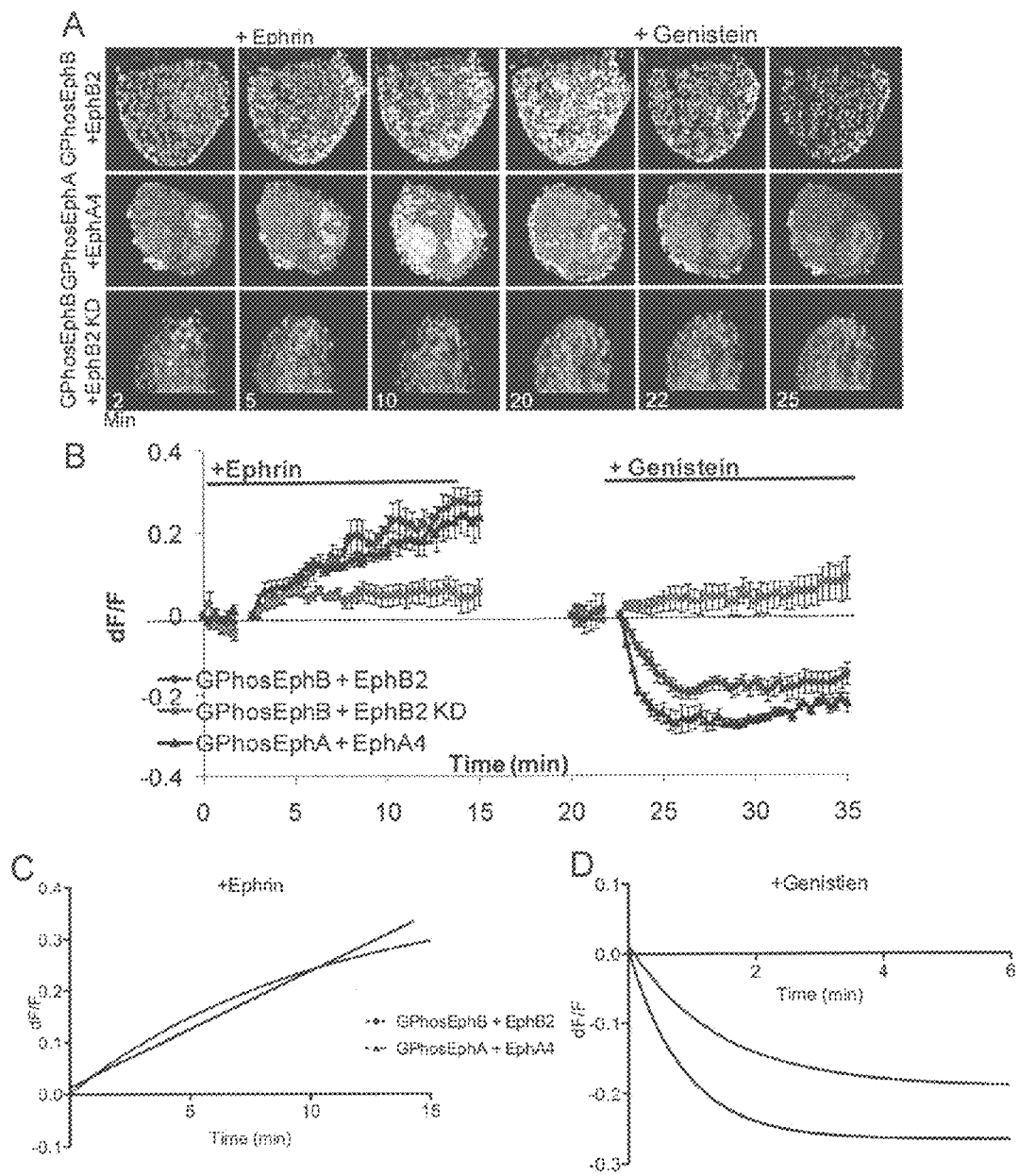
FIG. 11: The on and off kinetics of EphB2 and EphA4 receptor differ. A) Representative images of HEK 293T cells transfected with GPhosEphB and EphB2, GPhosEphA and EphA4, or GPhosEphB and kinase dead EphB2 (EphB2 KD). Treatment with appropriate Ephrin or the kinase inhibitor Genistein is shown by orange bar. Scale bar, 10 µm. B) Graph showing the change in ratio fluorescence after Ephrin treatment and after Genistein treatment. The same cells were subjected first to Ephrin treatment, then Genistien was added to the bath. Error bars indicate std error of the mean (n=7 (EphB2), 6 (EphB2 KD), 4(EphA4)). C) Kinetics of EphB2 and EphA4 receptor after Ephrin addition. Kinetic rate is a factor of both association and disassociation. One phase association Tau for EphB2=9.781, R square=0.9651 One phase association Tau for EphA4=9.602, R square=0.8717 D) Disassociation rate of EphB2 and EphA4 receptor after Genistien treatment. One phase decay Tau for EphB2=1.588, R square=0.9676 One phase decay Tau for EphA4=0.8484, R square=0.9921.

We have measured the activation and deactivation kinetics of kinases in cells. These experiments demonstrate that our indicators are able to report dynamic signaling. These results are consistent with reports and our own work showing that the Eph TKRs activate slowly. The activation rate we measure is on the order of 20 minutes (FIG. 11). To measure deactivation, we treat cells with a broad-spectrum tyrosine kinase inhibitor. This blocks TK activity and allows the indicator to be dephosphorylated and returned to its resting state. This approach would be suitable for use as a 'test agent' showing the deactivation of the indicators and enabling baselines for activity and inactivity to be established in an assay.

In summary, our indicators are ideally suited for uses as screening tools for compounds that act on TKs.

REFERENCES

Dalva M B, Katz L C (1994) Rearrangements of synaptic connections in visual cortex revealed by laser photostimulation. Science 265:255-258.
Dalva M B, McClelland C, Kayser M S (2007) Cell adhesion molecules: signalling functions at the synapse. Nat Rev Neurosci 8:206-220.
Dalva M B, Takasu M A, Lin M Z, Shamah S M, Hu L, Gale N R, Greenberg M E (2000) EphB receptors interact with NMDA receptors and regulate excitatory synapse formation. Cell 103:945-956.
Flanagan J G, Vanderhaeghen P (1998) The ephrins and Eph receptors in neural development. Annu Rev Neurosci 21:309-345.
Hirose K, Kadowaki S, Tanabe M, Takeshima H, Iino M (1999) Spatiotemporal dynamics of inositol 1,4,5-trisphosphate that underlies complex Ca2+ mobilization patterns. Science 284:1527-1530.
Honda A, Adams S R, Sawyer C L, Lev-Ram V, Tsien R Y, Dostmann W R (2001) Spatiotemporal dynamics of guanosine 3',5'-cyclic monophosphate revealed by a genetically encoded, fluorescent indicator. Proc Natl Acad Sci USA 98:2437-2442.
Irie F, Yamaguchi Y (2004) EPHB receptor signaling in dendritic spine development. Front Biosci 9:1365-1373.

Kaplan D R, Miller F D (2000) Neurotrophin signal transduction in the nervous system. Curr Opin Neurobiol 10:381-391.

Katz L C, Dalva M B (1994) Scanning laser photostimulation: a new approach for analyzing brain circuits. J Neurosci Methods 54:205-218.

Kawai Y, Sato M, Umezawa Y (2004) Single color fluorescent indicators of protein phosphorylation for multicolor imaging of intracellular signal flow dynamics. Anal Chem 76:6144-6149.

Kayser M S, Nolt M J, Dalva M B (2008) EphB receptors couple dendritic filopodia motility to synapse formation. Neuron 59:56-69.

Kayser M S, McClelland A C, Hughes E G, Dalva M B (2006) Intracellular and trans-synaptic regulation of glutamatergic synaptogenesis by EphB receptors. J Neurosci 26:12152-12164.

Mattila P K, Lappalainen P (2008) Filopodia: molecular architecture and cellular functions. Nat Rev Mol Cell Biol 9:446-454.

Miyawaki A, Llopis J, Heim R, McCaffery J M, Adams J A, Ikura M, Tsien R Y (1997) Fluorescent indicators for Ca2+ based on green fluorescent proteins and calmodulin. Nature 388:882-887.

Nakai J, Ohkura M, Imoto K (2001) A high signal-to-noise Ca(2+) probe composed of a single green fluorescent protein. Nat Biotechnol 19:137-141.

Oancea E, Teruel M N, Quest A F, Meyer T (1998) Green fluorescent protein (GFP)-tagged cysteine-rich domains from protein kinase C as fluorescent indicators for diacylglycerol signaling in living cells. J Cell Biol 140:485-498.

Pawson T (2004) Specificity in signal transduction: from phosphotyrosine-SH2 domain interactions to complex cellular systems. Cell 116:191-203.

Pologruto T A, Yasuda R, Svoboda K (2004) Monitoring neural activity and [Ca2+] with genetically encoded Ca2+ indicators. J Neurosci 24:9572-9579.

Robles E, Gomez T M (2006) Focal adhesion kinase signaling at sites of integrin-mediated adhesion controls axon pathfinding. Nat Neurosci 9:1274-1283.

Robles E, Woo S, Gomez T M (2005) Src-dependent tyrosine phosphorylation at the tips of growth cone filopodia promotes extension. J Neurosci 25:7669-7681.

Songyang Z, Shoelson S E, Chaudhuri M, Gish G, Pawson T, Haser W G, King F, Roberts T, Ratnofsky S, Lechleider R J, et al. (1993) SH2 domains recognize specific phosphopeptide sequences. Cell 72:767-778.

Takasu M A, Dalva M B, Zigmond R E, Greenberg M E (2002) Modulation of NMDA receptor-dependent calcium influx and gene expression through EphB receptors. Science 295:491-495.

Tallini Y N, Ohkura M, Choi B R, Ji G, Imoto K, Doran R, Lee J, Plan P, Wilson J, Xin H B, Sanbe A, Gulick J, Mathai J, Robbins J, Salama G, Nakai J, Kotlikoff M I (2006) Imaging cellular signals in the heart in vivo: Cardiac expression of the high-signal Ca2+ indicator GCaMP2. Proc Natl Acad Sci USA 103:4753-4758.

Timar J, Dome B (2008) Antiangiogenic drugs and tyrosine kinases. Anticancer Agents Med Chem 8:462-469.

Zaccolo M, De Giorgi F, Cho C Y, Feng L, Knapp T, Negulescu P A, Taylor S S, Tsien R Y, Pozzan T (2000) A genetically encoded, fluorescent indicator for cyclic AMP in living cells. Nat Cell Biol 2:25-29.

Ziv N E, Smith S J (1996) Evidence for a role of dendritic filopodia in synaptogenesis and spine formation. Neuron 17:91-102.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A genetic construct encoding a dual colored, specific, tyrosine kinase enzyme indicator molecule for assessing tyrosine kinase activity in a cell, said construct comprising the following sequences in operable linkage in the recited order:
   a) a promoter sequence effective to drive expression of said construct in a target cell;
   b) a sequence encoding a first fluorescent reporter molecule that is insensitive to changes in phosphorylation;
   c) sequences encoding at least two distinct consensus phosphorylation sites for tyrosine phosphorylation wherein the consensus phosphorylation sites are selected from the group consisting of SEQ ID NOS: 43-86;
   d) a sequence encoding a circularly permuted second fluorescent reporter molecule, where said first and second fluorescent reporter molecules fluoresce different colors; and
   e) an SH2 interacting domain from a tyrosine kinase selected from the group consisting of fyn, src, lck, Csk, p85, Ab1, RasGAP, Crk, Nck, She, FRS2, Grb2, SH2B, rAPS, PLC-g, Gab1, Grb7, Grb14, and yes, wherein phosphorylation of tyrosine in one or more of said consensus phosphorylation sites in c) causes said SH2 interacting domain to bind to said consensus phosphorylation site thereby causing the fluorescence signal of the second fluorescent reporter molecule to increase.

2. The genetic construct of claim 1 where the SH2 interacting domain is selected from the group consisting of fyn, src, RasGAP, Crk, and Nck.

3. The genetic construct of claim 2 where the SH2 interacting domain is fyn.

4. The genetic construct of claim 2 where the consensus phosphorylation sites are selected from the group consisting of SEQ ID NOS: 51-53.

5. An expression vector containing the genetic construct of claim 1.

6. An isolated host cell containing the expression vector of claim 5.

* * * * *